United States Patent
Morgan

(10) Patent No.: US 11,812,808 B2
(45) Date of Patent: Nov. 14, 2023

(54) HELMET INCLUDING IMPACT AND HEALTH DATA SENSING SYSTEM

(71) Applicant: Tate Technology, LLC, Pacific Palisades, CA (US)

(72) Inventor: Jenny T. Morgan, Pacific Palisades, CA (US)

(73) Assignee: TATE TECHNOLOGY, LLC, Pacific Palisades, CA (US)

( * ) Notice: Subject to any disclaimer, the term of this patent is extended or adjusted under 35 U.S.C. 154(b) by 448 days.

(21) Appl. No.: 16/945,585

(22) Filed: Jul. 31, 2020

(65) Prior Publication Data

US 2021/0030097 A1    Feb. 4, 2021

Related U.S. Application Data

(60) Provisional application No. 62/881,647, filed on Aug. 1, 2019.

(51) Int. Cl.
| | | |
|---|---|---|
| A42B 3/04 | (2006.01) | |
| A42B 3/30 | (2006.01) | |
| A61B 5/01 | (2006.01) | |
| A61B 5/00 | (2006.01) | |
| A61B 5/11 | (2006.01) | |
| A61B 5/0205 | (2006.01) | |

(52) U.S. Cl.
CPC .............. *A42B 3/046* (2013.01); *A42B 3/30* (2013.01); *A61B 5/01* (2013.01); *A61B 5/0205* (2013.01); *A61B 5/11* (2013.01); *A61B 5/1126* (2013.01); *A61B 5/6803* (2013.01); *A61B 2562/0219* (2013.01)

(58) Field of Classification Search
CPC ....... A61B 5/1126; A61B 5/6803; A61B 5/11; A61B 5/0205; A61B 2562/0219; A42B 3/30; A42B 3/046
USPC ........................................................ 600/301
See application file for complete search history.

(56) References Cited

U.S. PATENT DOCUMENTS

| | | | |
|---|---|---|---|
| 2007/0177651 A1 | 8/2007 | Daugherty | |
| 2013/0060168 A1* | 3/2013 | Chu | A61B 5/6803 600/595 |
| 2013/0110415 A1* | 5/2013 | Davis | A61B 5/6803 702/41 |
| 2015/0173666 A1* | 6/2015 | Smith | A61B 5/11 600/595 |
| 2017/0042272 A1* | 2/2017 | Ferguson | A42B 3/121 |
| 2017/0172243 A1* | 6/2017 | Scripa | A42B 3/303 |
| 2017/0238812 A1* | 8/2017 | Atlas | A61B 5/1117 |
| 2018/0110466 A1* | 4/2018 | Ralston | A61B 5/6814 |
| 2018/0235483 A1 | 8/2018 | Mouradian | |
| 2018/0295919 A1* | 10/2018 | Shearman | A42B 3/06 |

(Continued)

OTHER PUBLICATIONS

International Search Report and Written Opinion issued for PCT/US20/44641 dated Feb. 11, 2021.

*Primary Examiner* — Carl H Layno
*Assistant Examiner* — Michael J Lau
(74) *Attorney, Agent, or Firm* — Jeffer Mangels Butler & Mitchell LLP; Brennan C. Swain, Esq.

(57) ABSTRACT

A helmet configured to be worn by a wearer that includes an outer shell, an inner liner positioned inside the outer shell, a data collection assembly that includes a first data collection member for measuring impact data, and a second data collection member for measuring vital signs data.

16 Claims, 8 Drawing Sheets

(56) References Cited

U.S. PATENT DOCUMENTS

2019/0099114 A1  4/2019  Mouradian et al.
2019/0142286 A1  5/2019  Mouradian

\* cited by examiner

HELMET INCLUDING IMPACT AND HEALTH DATA SENSING SYSTEM

CROSS REFERENCE TO RELATED APPLICATIONS

This application claims the benefit of U.S. Provisional Application No. 62/881,647, filed Aug. 1, 2019, the entirety of which is incorporated herein by reference.

FIELD OF THE INVENTION

The invention generally relates to a helmet that includes an impact measurement and health data monitoring, collecting, and transmitting sensor system.

BACKGROUND OF THE INVENTION

Due to the seriousness of head injuries and resulting trauma, such as concussions, TBI and potentially CTE some current helmets include separate monitoring and communication systems. For example, some football helmets include devices that count impacts/hits. Current systems may transmit data if the RF transmitter has the ability to broadcast.

The background description disclosed anywhere in this patent application includes information that may be useful in understanding the present invention. It is not an admission that any of the information provided herein is prior art or relevant to the presently claimed invention, or that any publication specifically or implicitly referenced is prior art.

SUMMARY OF THE PREFERRED EMBODIMENTS

In accordance with a first aspect of the present invention there is provided a helmet configured to be worn by a wearer that includes an outer shell, an inner liner positioned inside the outer shell, and a data collection assembly that includes a first data collection member for measuring impact data, and a second data collection member for measuring vital signs data. In a preferred embodiment, the inner liner defines a liner interior and the data collection assembly includes a vital signs sensor. The data collection assembly is positioned such that vital signs sensor is open to the liner interior, such that when the helmet is worn by the wearer, the vital signs sensor is positioned adjacent the wearer's skin. Preferably, when the helmet is worn by the wearer, the vital signs sensor is positioned adjacent the wearer's temple region.

In a preferred embodiment, the vital sign data includes one or more of blood pressure, oxygen saturation, heart rate, respiration rate, skin temperature, and EKG, and wherein the impact data includes one or more of g-force, linear acceleration, rotational acceleration and pitch changes, roll changes and yaw changes. Preferably, the first and second data collection members are housed in a first housing that is received in a pocket defined in the inner liner. In a preferred embodiment, the first and second data collection members are housed in a first housing that is received in a recess defined in a bracket that is positioned in a pocket defined in the inner liner. In an embodiment, the data collection assembly includes a third data collection member for measuring impact data that is positioned outside of the first housing (and elsewhere in the helmet). Preferably, the first housing is removable from the recess. The vital signs sensor may include at least one optical emitter and at least one optical receiver.

In accordance with another aspect of the present invention there is provided an impact monitoring system that includes a helmet that includes an outer shell, an inner liner positioned inside the outer shell, and a data collection assembly that includes a first data collection member for measuring impact data, and a second data collection member for measuring vital signs data, and a software application executing on a mobile electronic device in data communication with the data collection assembly. When the impact data is at a predetermined threshold an impact safety alert is generated. In a preferred embodiment, the impact monitoring system further includes a server (or other computer or the like) in data communication with the mobile electronic device, and wherein the impact safety alert is generated via the server.

In a preferred embodiment, the impact data includes a g-force measurement, and if the g-force measurement is above a predetermined threshold a g-force measurement safety alert is generated and when the vital signs data is at a predetermined threshold a vital signs safety alert is generated.

The present invention uses a sensor system to collect data related to impact force at the point of compression in the helmet shell versus in tension. The system includes sensors or data collection members that include accelerometers that measure the g-force on the x, y & z axes, plus gyros that measure pitch, roll and yaw triaxial measurement. The sensor system also includes capture of key health bio-metrics/vitals that are continuously monitored real-time from the player during the activity that are compared continuously against resting data. The system is designed to provide doctors, medics, and trainers either on the sidelines or remotely who are receiving the data on a tablet or computer, to be able to recognize changed key bio-metrics/vitals that demonstrate prospective impairment to the health of the player. The bio-metrics coupled with the actual g-force taken at compression provides data in order to make a decision on when to pull a player for a potential concussion or other health related issue(s).

The present invention relates to an at compression impact g-force measurement, plus bio-metric vitals data capture, measurement, and communicative sensor system for acquisition, transmission, and analysis of recorded real-time bio-metric and other key vital data attained during athletic or other activities from impacts, recorded against benchmarked bio-metric health measurement data. Data is gathered from impact-based or compression blast force related to athletic and military activities respectively addressing impact(s) from contact, as well as non-contact sports, provided by an impact engaging element(s) or sensor(s) with impact force accelerometer elements, which are either strategically incorporated or placed in predetermined location(s) at the point of compression or point of impact embedded in the helmet shell, or immediately attached on the inside of the helmet shell, or the sensor system may be strategically placed next to the wearers temple region and via use of Bluetooth capture of the impact force using pre-set algorithms, or the sensor system may be strategically placed next to the wearers temple region using a connective wire extending from the sensor system attached to the interior of the helmet shell, or finally a soft headwear element prospectively assisting the wearer(s) incurring destructive impact or g-force through daily athletic activities or other activities, as well as the military, construction, etc. The bio-metric sensor(s) is/are strategically positioned anywhere inside or incorporated into the helmet shell, but may be placed, in particular, adjacent to the wearer(s) left or right temple region, and potentially in an additional location on the wearer to capture bio-metric data, which, for example could be in the wearer's neck region next to, near or on the carotid artery.

The present invention relates generally to an "at compression" data sensor capture technology system for general helmetry and soft headwear use in sports that utilize helmets and soft headwear for impact protection designed to protect the brain from injury resulting from a single incident to repetitive impact force to the wearer's head in sports, military, construction & industrial, and police/riot, and others. The present invention includes sensor(s) in an arrangement to capture impact force to address impact mitigation of the wearer through repetitive impact with the ground, objects, other players, etc. and motion resulting from use. The invention also includes data sensor(s) and system(s) to provide real-time biometric data and feedback with specific vitals biometric information of the wearer to a database and/or first responders.

The sensors may also provide additional impact, physical, and vital information using the sensor(s) system(s), which is/are used to determine impact g-force, as well as tracks physical vitals normally taken at the doctor's office or hospital, as well as athletic tracking of the number of steps, activity levels, and finally potential fall or tripping, pitching detection to alert others of the individuals mishap, plus more. Encryption can be provided in military defense settings or environments, so enemy combatants will not be able to track the military personnel's location.

By measuring g-force of impacts sustained to the head, data is collected that can lead to prevention of concussions and further brain damage. Integrating the data collected from impact sensors into reporting software will greatly aid the medical professional in tracking impact severity and medical complications potentially indicating a concussion, and track over time the players medical history and progression, e.g., over the athlete's career.

One of the purposes of the invention is to monitor impact force at the point of compression. The present invention allows monitoring of impact force at impact, or at compression in the helmet shell versus in tension, which is fundamentally different. At impact is the occurrence at the helmet shell where the peak severity index, or SI is measured at its highest intensity. As impact force travels through the helmet shell, through the liner system(s), followed by going into the brain it has different measurements of the severity of impact force—for example the SI measures the initial peak impact, g-force measures the amount of impact force, and the Head Injury Criterion or HIC measures the severity of the impact to the brain. The purpose of the present invention is to measure the impact at compression versus later in tension and then comparatively analyze the difference of the peak severity index at compression versus tension and note the full and initial impact force at the point of occurrence.

Numerous "in-lab" and "field" tests are being conducted using prior art systems and to truly understand the nature of the impact force there needs to be complete measurement of all the metrics from the peak of the impact incident. The at compression data sensor capture technology system of the present invention also provides additional impact, physical, and vital information using the sensor(s) system(s). For example, the technology disclosed in U.S. Publication No. 2019/0099114 (the "'114 publication"), and/or U.S. Publication Nos. 2018/0235483 and 2019/0142286 the entireties of which are incorporated herein by reference, can be used in the present invention. The sensors and related technology taught in the patent applications referenced above can be used to determine, for example, impact force, as well as track physical vitals/bio-metrics normally taken at the doctor's office or hospital, as well as athletic tracking of the number of steps, activity levels, and finally pitching, potential fall or instability detection to alert others of the individuals mishap. Falling, or instability detection (using any of the sensor, sensor systems or other components disclosed herein) may be useful to determine if a player has suffered a concussion by the sway, pitch, or loss of balance of the torso, chest area or head of the player compared to a pre-set and a certain degree change measured at a walk, jog, stand, or run. This is perceived to be unique as to actual play, which is a more "determined" motion, or action (versus swaying), which is uniform in motion and constant. All bio-metrics captured real-time during play may be collected using Bluetooth technology with line-of-site up to or beyond 1,000 feet. Data is collected continuously and tracked against each player or wearer's benched resting biometrics already in the database. In a preferred embodiment, the system includes a cloud-based computer, tablet and mobile phone-enabled vitals monitoring system, which may be referred to herein as "Sideline Bio-Metrics Monitoring Technology." These include, but are not limited to the following measurements: Blood Pressure, Heart Rate, SpO2 (Oxygen Saturation), Respiration Rate, ECG/EKG (electrocardiogram), temperature, historical and trending data, alerts from deviations of set thresholds, hydration alerts, stress alerts, activity, step count, calorie count, calendar, sleep quality, nutrition, and medication reminders, skin temperature, fall detection, algorithm written per product application and design, accelerometers to measure g-force at compression, gyros for various applications, out of range alerts, cloud back-up and transmission, geo location, alerts dashboard and emergency response system, notifications and alerts to set contacts via text, email, call, cognitive behavioral health, memory analysis, alerts for deviations from normal activity, machine learning, chronic disease care, diabetes, COPD, CHF, pain management, hypertension, and stroke alerts.

The basis of the at compression impact and health data sensor capture technology system of the present invention model comprises a sensor system dynamic consisting of accelerometers in the helmet shell, or at the point of compression to measure g-force of the impact, and/or using Bluetooth directly capturing impact force at compression, or at the point of impact.

The present invention also includes an integrated micro or nano impact crash, activity, and vitals sensor(s) data unit to track not only g-force, but also initial impact, i.e., Severity Index. Additionally, key vitals may also be tracked with an impact crash and vitals sensor(s) system in the helmet with a sensor(s) system that may be attached into the liner system next to the skin at the left temple region, neck region, and more that can measure blood pressure (BP), oxygen saturation rate (SpO2), heart rate (HR), respiration rate (RR), skin temperature, EKG, and more. Finally, the same system may have pitching, fall or tripping detection, activity level, distance, location and altitude, speed, step count, and more. The insert is designed to fit within the prior art or existing helmet systems. The sensor(s) system(s) is used to determine impact force, as well as may track real-time physical vitals normally taken at the doctor's office or emergency room or in the hospital, as well as balance, and athletic tracking of the number of steps, activity levels, and finally potential fall or tripping detection or sensing to alert others of the individuals falling likely due to hard impacts and potential sub-concussive to concussive impact force.

One of the objectives of the present invention is to provide an impact sensor system to detect impact force "at compression," or at the actual point of impact (at a point in time and/or at a specific location) the point of greatest force measured. Additionally, the objective of the present invention is to track real-time player/wearer bio-metrics capturing data and changes to players on a continuous basis relating directly to/against already measured resting bio-metrics entered into the database as a baseline benchmark. This addresses immediate tracking of changes in measured bio-metrics to be monitored, and to be evaluated in real-time on the sidelines in sports, etc. with doctors reviewing (whether or not they are physically present tele-health availability on demand via the Cloud technology). Alerts are built in using algorithms, pre-detection measurements per athlete/wearer, as well as pre-set measurements on g-force wider range than currently used in the prior art related to each respective sport or discipline known to the prior art. Sensitivity to the level of sub-concussive hits will be evident in the measurement of real-time bio-metric tracking, which the data is immediately registered and comparative analysis is provided, plus accumulated data is maintained or stored in the software and Cloud in order to better perfect and measure the reality of impact and force on the human body and the resulting changes in key bio-metrics measurements. The present invention may also include micro or nano technology to track the following: g-force and initial impact severity, as well as some or all of the following: also key vitals, such as blood pressure, oxygen saturation rate, heart rate, respiration rate, skin temperature, EKG, as well as fall detection, activity level, distance, location and altitude, speed, and step count.

The present invention has full administrative functionality, as well as tiered levels of access to confidential information for patient protection. The present invention is also HIPAA secure Cloud views and data protection. The present invention also has Machine Learning. The present invention is also FDA approved, for BLE medical devices. The present invention is also multi-party video and audio with customizable 'One touch access to 211 service line' HIPAA security and privacy provisions.

The present invention is also streaming vitals and access to historical data with secure messaging between patients/players/wearers and medical care teams. The present invention also monitors and set alerts with push notifications. The present invention also tracks time spent per patient for appointments, diagnosis, follow up, prescriptions, data entry. The present invention also offers New Remote Patient Monitoring, or "RPM. CPT codes—all are available if desired to be used in the present invention's application.

Considering the number of parameters contributing to monitoring vitals post impact the system will be able to provide accurate real-time biometrics data sent continuously throughout play to the sidelines and to any selected medical professional, hospital, etc. to monitor the continuous real-time data.

The present invention at compression impact and health data sensor capture technology system(s) is formed with one to several sensors to include impact data collected via accelerometers, but at the point of "impact or compression" in/at the helmet shell next to the wearer's head, and preferably at the left or right temple region of the wearers head. There may be a second or additional sensor to capture all relevant bio-medical health monitoring data from the wearer for real-time transmission of data to the sidelines and/or remotely to doctors and/or hospitals related to stored benchmark of the wearer's bio-medical health data already in the software. The one or more strategically placed accelerometers and gyros will track and send real-time transmission via Bluetooth and the Cloud the impact force and other impact measurements, such as the initial impact force, or Severity Index, as well as in both linear and rotational acceleration, velocity, and deceleration, pitch, roll, yaw, and the health sensor shall address the significant changes to the wearer as a result of the impact force medically speaking. As an example, the helmet shell may have the impact sensor(s) either embedded into the shell at formation, whether it is injection molded, or in a lay-up fabrication helmet, or just on the inside of the helmet shell. The medical capture sensor(s) may be located immediately next to, making contact, and touching the wearers left temple area on the side of the forehead contained in one or potentially more micro location (s) (the size of a nickel) of the entirety of the liner insert system. One sensor may be used since it contains all force measurement accelerometers, gyros, as well as health capture, measurement using Bluetooth, and analysis soft and hardware using code and algorithms.

The sensor(s) preferred embodiment capture system materials is solely a prefabricated chip that acts independently and not being tied or tethered with leads or wires, and is completely Bluetooth capable sending data real-time to the application downloaded on a computer, tablet, or phone, etc. used by teams on the sidelines. Leads may be used. "Teams" meaning a physician, or additionally a nurse, paramedic, trainer, etc. in conjunction with an off-site physician. The dimensions of the chips are comparable to a nickel to quarter in size and depth. The sensor(s) or chip is housed in a bracket and it is exchangeable between helmets outfitted with holding brackets to house the sensors, etc.

The entire sensor capture system's materials may also include a plastic bracket to house the sensor(s). The bracket's function is to house the sensor keeping it exactly positioned at compression and or next to and continuously touching the wearers head in the temple area/region. It is able to withstand impact force, temperature changes also ensuring proper stability in function.

The entirety of the at compression impact and health data sensor capture technology system(s) embodies an inherent impact capture of the amount of g-force, the number of hits, the amount of sub-concussive to concussive measurements, and health monitoring system that is deployed over the helmet shell, or at compression, along with the resultant bio-metric/vitals data measurement taken from the wearer from the left temple region, which is real-time continuously benched against resting bio-metrics in software loaded into a computer, laptop, tablet, phone, etc. sent via Bluetooth and the Cloud. It is an at compression data sensor capture technology system and apparatus that is designed to analyze medical bio-metric vitals data the wearer undergoes from one time and/or repetitive impacts derived from training, practice competition, or any physical sport activity where the head may be directly impacted. The current invention is designed to measure how g-force acts on the wearer and the wearer's bio-metrics tracking in real-time, and providing the medical basis with medical analysis, also real-time whether present or remote when a player should be removed with true diagnostic analysis and results versus the current non-medical data-supported review by trainers, and other non-medical professionals on making a determination when to pull an athlete from the field of play. The current invention, as a protective and preventative data capture and management for at compression impact and health data sensor capture technology system(s), includes sensors used in the medical, and geriatric fields with application in sports and military fields in combination with measuring g-force at compression versus in tension, and in combination monitoring the wearer with real-time data as they play their sport, or on the battlefield. One impact or health sensor will be placed next to the wearer's skin in the left temple region, and if required additional impact or accelerometer sensor(s) will be embedded in or placed immediately behind the outer helmet shell comprised of polycarbonate, ABS, or lay-up helmets using carbon fiber, fiber glass, or composites of all the above materials. The health measurement sensor and if required potentially the additional impact or accelerometer sensor(s) will be to capture the amount of impact force achieved with medical bio-data read real-time at the point of impact at compression, or at the moment of the hit to the wearer's head, and the resulting impact on the wearer from the hit, which takes a true hit index measurement to the wearer versus in tension where prior art systems reside that are located or positioned right next to the wearers head. In tension, where current systems reside, the impact force is different, as the liner, whether it is padded material science, air, fluids, suspension, or a combination of the above spreads the impact force over distance and time thereby changing the peak severity of the impact metric—the real impact force at compression is the true amount of force of acceleration and deceleration physics, and while the padding shock absorbs these do not convert energy to heat in order to truly energy attenuate.

The health measurement sensor(s) may be located immediately adjacent and touching the wearers head at the left temple region. Sensor(s) will be housed in a plastic bracket, and the additional sensor(s) to capture g-force will be housed in a plastic bracket on the inside of the helmet shell or potentially embedded in the lay-up helmet or in the injection molded helmet process. The first sensor will be housed in a plastic bracket that will be incorporated into the liner system(s) located next to the left temple of the wearer in the helmet system. The sensor will have an outer surface, an inner surface and a cylindrical surface with a front region to be located next to the point of impact and next to the wearer's head/temple, a rear region, and a round side region. The bracket will have an inner surface, and outer surface, a closed square, rectangular, circular, or cylindrical side surface that will house the sensor(s).

The present invention may only need to use one sensor residing by the wearer's head or temple region using Bluetooth to detect impact force that will not be impeded by material science of layers in the liner system. The present invention may use more than one sensor strategically placed throughout the helmet system to capture the impact or g-force, and the health sensor may also have tangentially more than one location.

The present invention is further comprised of and encompasses a software system to capture and analyze the data, transmit the data via the Cloud real-time, data transmittal real-time with 1,000 feet unimpeded transmission, compare the data already benched and stored in the software containing resting bio-metrics. The data may also be sent real-time to off-site medical personnel to read the data for analysis—this will be the premise for youth sports where there is limited budgets to support an on-field medical person, paramedic, or trained medical professionals, etc. Trainers are not necessarily educated to support this function, so a medical designated person will be on notice during the times required and notified real-time when data dictates necessity of their professional diagnosis and review. The software provides a wide variety of important medical diagnostics normally taken or checked at your doctor's office, the emergency room, etc. that provides doctors key real-time bio-metrics and compared to the benchmarked resting and/or activity data, whether physically present or off-field, or off-location, with strong data to analyze on whether or not a player should be removed based upon proven bio-metric/vital changes to the players conditions to prevent further health issues at the immediate time, and further in time in a person's life cycle. The inventive method and apparatuses sensors and systems seek to mitigate the immediate and long-term propagation of the damage resulting from highly linear and nonlinear (rotational) impact force.

The present invention further comprises an improved impact measuring system with use of "measuring impact at compression," taking into account the impact properties of the "waveform(s)" of both linear and rotational impact force. Impact force at compression undergoes full contact between two objects one or both may be moving, with the transfer of energy, and "during an impact, the energy of a moving object is converted into work, and force, which plays an important role. To create an equation for the force of any impact, you can set the equations for energy and work equal to each other and solve for force. From there, calculating the force of an impact is as follows: divide kinetic energy by distance. $F=(0.5*m*v^2) \div d$. Impact and Energy—Energy is defined as the ability to do work. During an impact, an object's energy is converted into work. The energy of a moving object is called kinetic energy, and is equal to one half of the object's mass times the square of its velocity: $KE=0.5 \times m \times v^2$.

When thinking about the impact force of a falling object, one can calculate the energy of the object at its point of impact if you know the height from which it was dropped. This type of energy is known as gravitational potential energy and it is equal to the object's mass multiplied by the height from which it was dropped and the acceleration due to gravity: $PE = m \times g \times h$. Work occurs when a force is applied to move an object a certain distance. Therefore, work is equal to force multiplied by distance: $W = F \times d$. Because force is a component of work and an impact is the conversion of energy into work, you can use the equations for energy and work to solve for the force of an impact. The distance traveled when the work is accomplished by an impact is called the stop distance. It is the distance traveled by the moving object after the impact has occurred.

Impact From a Horizontally Moving Object—Now to calculate the impact force of a 2,200-kilogram car traveling at 20 meters per second that crashes into a wall during a safety test. The stop distance in this example is the crumple zone of the car, or the distance by which the car shortens on impact. Suppose the car is collapsed or crumpled enough to be three quarters of a meter shorter than it was before the impact. The first step is to set the equations for energy—this time kinetic energy—and work equal to each other and solve for force. W=KE is $F \times d = 0.5 \times m \times v^2$, so $F=(0.5 \times m \times v^2) \div d$. The final step is to plug the values from the problem into the equation for force: $(0.5 \times 2,200 \text{ kilograms} \times (20 \text{ meters/second})^2) \div 0.75 \text{ meters} = 586,667$ Newtons."

Collision physics continued illustrated with helmets: The weights of each helmet and head are the same-16 lb., and each are traveling at 15 mph (22 feet per second) toward each other, with a helmet structure thickness requires that it can only deflect one inch in this collision. From basic physics for uniform acceleration: Acceleration=Velocity squared, divided by twice the distance ($a=v^2/2d$), $a=484/0.167=2900$ ft/sec.$^2$ The time of this deceleration is calculated from: Time=velocity/acceleration. Time=22/2900=0.0076 seconds=7.6 milliseconds. Therefore, at the moment of impact, each helmet will undergo 90 gs of deceleration (about 2900 feet per second squared) lasting for a period of 7.6 milliseconds, assuming that the deceleration is uniformly spread over the collision. Note: the decelerating force is far from constant in any accurate helmet calculation. This means that the deceleration calculated above is only the average and that unfortunately the peak deceleration experienced is certainly somewhat higher than this average. The force in pounds applied to each helmet during this collision is simply F=m*a, the mass (in "slugs"=weight in lbs divided by 32) of the helmet and its contents times 2,900. This force is therefore 1,450 lb. applied for 7.6 milliseconds, again with the simplifying assumption of uniform deceleration.

Relative to the "knowns" of what impact force, repeated impact force, and from sub-concussive to full-blown concussions does to the human body, it is important to monitor, track, and benchmark the impact and change to the human body. All metrics, such as elevated heart rate, increased blood pressure, reduced oxygen saturation, fluids & swelling, EKG, respiration rate, and so on indicate the human body is under stress proportional to normal conditions of resting or activity that is not incurring harmful impact force. Looking at the type of collisions from a physics standpoint—in the 'inelastic' collision the kinetic energy is dissipated as heat. Also remember that a human head is hard/soft, so that even if a deforming substance on the outside of the head could transform completely into heat the soft brain still decelerates into the hard boney skull. The real observation of a deforming substance used to interact with the collision mass and velocity is this: upon initial contact a high rate of deceleration will occur, but this rate of deceleration decays as the substance deforms, it's the nature of the deforming substance as an 'inelastic collision' that determines the decay time factor of the absorbent material used for the deforming interactions occurring during the collision. During an 'elastic' collision it's like the classic steel balls suspended touching each other apparatus, called Newton's Cradle. If the first ball is raised then released all the energy transfers through each ball swinging into each immediate neighbor's steel ball. If the collision is completely elastic without any energy being absorbed the velocities of the helmets instead of steel balls (human heads) are exchanged. The elastic collision is like two rams butting heads, they jar backward, stunned, as the impact speed turns into the rebound velocity, with virtually no kinetic energy transformed into heat except if the horns engage and stick their friction would become heat. This situation is the worst for both rams and for two colliding helmeted football players since the transfer from impact into rebound force lasts twice as long. During this delay the brain sloshes into cranial bone deforming/shearing in the coup/contre-coup brain rebound. Most helmet hits are neither perfectly elastic or inelastic.

Since the application of the present invention will be working with existing hard exterior helmet shell materials, as well as with soft liner system materials with which to hold the plastic brackets, or soft headwear with brackets containing the sensor(s), the robustness of the plastic housing and the sensor(s) are key in working within the measurement of impact force, and are themselves able to withstand enormous g-force maintaining the integrity of the system with the forces applied. No changes will occur with force to the dynamics and robustness of the housing and the sensor throughout the duration and lengthy life cycle of the sensor. The physics alone of impact force is proven damaging to not only the wearer or player, but also the materials used in protective gear, and the housing and sensor can withstand repeated significant impact forced incurred in football, the military, motorized sports and more. The continuity of the materials, which have been tested and are used today can withstand high velocity impact force with strain and shear rates that are tremendously destructive.

The present invention will also address the time transition of impact force and what it does to the wearer's body as it moves from compression through tension and into the wearer's head. Acceleration and deceleration through mass is in relationship to the intensity of the impact force with resultant dynamics of impact force upon the wearer's head and body. The current invention will also address the pitching, or pitch, roll and yaw of the wearer after impact, plus the current invention also addresses g-force measured for the first time at compression.

The synopsis herein represents a summary of aspects of the invention to provide a basic understanding of the invention, and the purpose of the invention. This summary provides an overview of the invention, and is not intended to identify all key critical elements of the invention, or to define/describe the scope, capacity or opportunity of the invention. The summary simply provides some concepts of the invention in a general form, as an introduction to the comprehensive description outlined below.

Aspects of the invention pertain to at compression impact sensor(s) measuring g-force and health data sensor(s) capture technology system, which could be one sensor data receiving or sending devices, and holding bracket device(s), which include(s) respectively for the impact measurement and health data system(s) a base member, a top member, and a circular side member; and for the bracket member a top member, a base member, snap-in member(s), and a complete square, rectangular, oval, or circular member, all of which hold the health sensor(s) device, as well as the bracket device(s) respectively are or act as two engaged or connected units for function. The one complete unit, engaged as a health capture data system. The additional sensor(s) if required are located "at compression" where impact force is measured at the point of impact or the point of compression versus in tension, and/or may be measured using Bluetooth inherently built into the sensor(s) system, or by leads or wires connecting the sensors. The data capture system is to be applied as a health and impact force measurement unit system. The sensor casing may be made of steel, titanium, carbon fiber, aluminum, or other metal and other materials as used in the prior art. The sensors are reusable and may be transferred from helmet to helmet or soft headwear to soft headwear. The sensor bracket member(s) may use materials, such as impact resistant plastic, such as Polycarbonate, ABS, or other "plastic" materials used with a cavity to house or contain the sensor(s) therein. The bracket insert member(s) may also include or define a cavity, or cavities, numerous voids to house or hold the sensor(s). The sensor(s) member(s) house or include a computer circuit board that captures all the following metrics and more including: vital signs/derivatives such as blood pressure, heart rate, oxygen saturation, respiration rate and skin temperature; enhanced vital signs, such as EKG, galvanic skin response, hydration, chronic disease management and alerts and pain level (provided by user); fitness tracking, such as activity level, ambient temperature, cellular head set, distance, fall detection, location and altitude, speed and step count; and impact force measurement, such as g-force and severity index.

The sensor(s) may also include specific algorithms designed for this present invention, and may also include an impact crash and vitals sensor(s) system(s) to include data capture including, but not limited to: include an integrated micro or nano impact crash and vitals sensor(s) unit to track not only g-force, but also initial impact i.e. severity index, or "SI." Additionally, key vitals may also be tracked with an impact crash and vitals sensor(s) system in the sensor(s) system with a sensor(s) system that may be attached onto the skin or resting next to and touching the wearer's skin at the left temple that will measure blood pressure, oxygen saturation rate, heart rate, respiration rate, skin temperature, EKG, and more. Finally, the same system has fall or tripping detection, activity level, distance, location and altitude, speed, step count, and more.

One feature of the present invention, is directed to the sensor(s) insert member, or specifically to the bracket housing or holding the sensor(s) member structure for sensor insert, the bracket structure comprising an outer member and a plurality of other outer members designed to securely hold the sensor(s) right next to the wearer's left temple, and the stability of the sensor(s) being held in place is also assisted by the helmet system with proper fit. The sensor is fully integrated into the wearer's helmet system and immediately engaging with the software on the sidelines held in a phone, tablet, laptop, computer, or some other hardware device that houses the software application and will capture real-time data transmitted by the sensor(s) housed in the wearer's helmetry system.

Another feature of the present invention is directed to the sensor itself, including a top or upper member, a base member structure, the circular or continuous round side member, the computer member, the accelerometer(s) member(s), the gyro(s) member(s), the Bluetooth member(s), the radio frequency for transmission members, the ability to transmit data via/using the Cloud services member, GPS, the mathematical formulas or algorithms members designed for the capability of the present invention, the longitude or latitude members, and the proximity awareness member. The base member structure includes an outer member and a plurality of a smooth impact engaging surface members designed throughout the base portion of the outer member. The top member structure includes an outer member and a plurality of a smooth impact engaging surface members designed throughout the top portion of the outer member. The continuous circular side member structure includes an outer member and a plurality of a smooth impact engaging surface members designed throughout the circular or side portion of the outer member.

Another feature of the invention is the plurality of the impact and health engaging members include a first impact and health engaging member in the base of the sensor(s) system, a second impact and health engaging member in the top of the sensor(s) system, and the third impact and health engaging member in the continuous circular or side member of the sensor(s) system, attached to or housed within the bracket system member. The plurality of members is unified into one member complete unit included and bounded by the first, second, and third engaging members.

Another feature of the invention where the first impact and health engaging member, the second impact and health engaging member, and the third impact and health engaging member, and so on will also partially exhibit an impact capture motion through the use of the accelerometer sensor and gyro sensor members.

Another feature of the invention is the plurality of all impact and health engaging members includes a second impact and health engaging member, where the entire second or top member is a second impact and health engaging member, which may also be termed as an apex. The second impact and health engaging member includes a first design and a second design, where the apex has a first height with respect to the base portion in the first design to follow the base design of the wearer's left temple. The height of the system may not be greater than the second height, where there is a subtle transition, not hard angled edges between the apex height and the base member. All impact and health engaging structure(s) at least partially comprises an impact resistant structure in the use of steel, aluminum, titanium, graphene, carbon fiber, etc., and other material.

Another feature of the invention is the impact and health engaging member sensor system where the first, second and third impact and health engaging members in the sensor system, where the entirety of the three members reside within the bracket structure system that includes an outer member, and inner member, and closed square, rectangular, oval, circular side members enclosing a plurality of the impact and health engaging member(s) sensor in the form of plastic material where the bracket unit member engages the plurality of the first, second, and third members of the entirety of the impact and health engaging sensor system. The plurality of the first or base impact and health sensor system member also engaging the plurality of the bracket member(s) comprise at least a first transition member between the plurality of the impact and health engaging sensor system member and the bracket member.

Another feature of the invention is the plurality of the impact and health engaging sensor system members that will have an outer member, an inner member and circular or side member(s) enclosing the computer sensor system where the top member will engage with the wearer's left temple region of the head. The first, second, and third impact and health engaging members are joined at an apex where at least partially a portion of each impact engaging member overlaps and is fused, glued, spot welded, or chemically sealed to seal and protect the plurality of these members to form the "sensor" system that engages with impact force as well as reads the wearers bio-metrics. Another feature of the invention is the plurality of the leads or wires if required, and another feature of the invention is the use of Bluetooth wireless transmission. Another feature of the invention is the plurality of the impact crash, activity, and vitals sensor(s) system(s).

Sideline bio-metrics readings for athletic activities using sensors that read not only impact force at the point of compression, but also capture all the bio-metrics that your doctor or the emergency room will read and monitor of a patient benched against resting bio-metrics entered into a software held in a hardware device on the sidelines of the sporting activity. The bio-metrics will be monitored real-time throughout the duration of play, be registered into the software for real-time review with alerts for the medical personnel on the sidelines, or that is transmitted real-time using the Cloud to a medical person or doctor remotely at a hospital or other location for immediate expert medical analysis and determination if the athlete should remain in the play at that activity. The data is real-time transmitted during the activity to the sideline.

A bio-metric data capture and communicative sensor system measurement device system for acquisition and analysis of recorded real-time bio-metric and other key data attained during athletic or other activities, recorded against benchmarked bio-metric health measurement data, resultant from impact-based or compression blast force injuries, especially relating to athletic activities addressing impact(s) from contact, as well as non-contact sports, is provided by an impact engaging element(s) or sensor(s) with impact force related energy or impact accelerometer elements, which are strategically provided in predetermined location(s) at the point of compression or point of impact in or immediately attached on the inside of the helmet shell, or soft headwear element prospectively assisting the wearer(s) who incur destructive impact or g-force through daily athletic activities or other activities, such as the military, construction, etc. The bio-metric sensor(s) are strategically positioned immediately next to the wearer(s) left temple region on the head, and potentially in an additional location on the wearer to capture bio-metric data, which could be in the wearer's neck region next to the carotid artery. Bluetooth may eliminate the use of placed sensors in or at the helmet shell.

The energy capture recordation and measurement designed in the sensor system includes in the accelerometers and gyros algorithms designed specifically that are actuated at the point of impact or at the point of compression versus tension to capture the force of the impact by means of the real-time sensor properties of the sensor systems.

The method of the present invention embodies an inherent energy impact capture and bio-metric measurement system contained in a closed/sealed sensor(s) system comprised of sensors that contain accelerometer(s), gyro(s), algorithm(s), software, hardware, programs, applications, and more designed to read impact force at the point of compression versus tension where current and prior art systems measure g-force right next to the wearers head, and to capture bio-metric data at impact and translate to the sidelines real-time for analysis against the wearer's pre-recorded and benchmarked bio-metric data. The sensors are made out of impact durable and resistant materials able to withstand impact force, temperature changes also ensuring proper stability in function, in a permanently enclosed environment to capture, read and measure impact forces, as well as bio-metric data of the wearer resultant from the impact and benched against pre-recorded resting bio-metric data of the wearer. The present invention is designed to not only read g-force from impacts, and at compression versus in tension as the prior art does, but also to read the wearers bio-metric vital data to compare what happens to the wearer at impact and compare against pre-recorded bio-metric vital data to see the resulting changes in bio-metrics with alerts to the wearer as a result from the impact g-force. The present invention is an at compression data sensor capture technology system and apparatus that is designed to provide the medical personnel and the wearer with the key noted changes to the wearers body that occurs as a result of impact g-force and prospective injury resulting from the impact force. The data analysis performed on the sidelines or real-time using the Cloud to medical personnel is also designed to provide medical professionals with real-time bio-metric vital data to medically assess the wearer's medical competency of continuing with the athletic or other endeavor. The present invention using one or more sensor engaging members contained in the helmet shell and next to the wearer's left temple region or more, with the sensor(s) containing outer and inner layers using aforementioned material(s) to contain the sensor(s) and maintain the sensor(s) in a protective environment to withstand impact force whether it be one time significant impact force or multiple, or continuous impact force using aforementioned material(s) system to house the "sensor(s)" to capture, read, measure, and relay the impact force information and bio-metric vital data resulting from contact at the point of compression in a wearer's helmet or soft headwear, or for other similar use.

The method embodies a sensor(s) system that is activated by the impact force at compression versus in tension coupled with the algorithms and designed software and headwear sensor system contained within the outer and inner layers of the three engaging impact capture members system of the sensor system resulting in capture, read, communication of real-time impact force and data at the point of impact, or compression.

The present invention looks at a wearer's impact capture at compression along with bio-metric vital data capture sensor system for medical review against pre-recorded resting benchmark bio-metric data from impact-based injuries, especially relating to repetitive activities, is provided by three engaging impact members of the sensor(s) system with outer and inner material/element/members, with a circular surrounding member that houses within the sensor system and contains the accelerometer(s), gyro(s), algorithm(s), software, hardware, programs, applications, and more designed to read impact force at the point of compression. The computer hardware system design is strategically provided in the entire three engaging impact member(s) contained within the outer and inner layers of the sensor system, which is then also securely contained within the bracket insert with outer and inner material/element/members designed to house and hold the sensor(s) system, and for providing the wearer with data designed to assist the medical personnel to read, review, and analyze the captured bio-metric vital data, and make informed decisions of the resultant injuries related to impact during daily use of sports, or other similar activities, as well as for the military from compression blast force, and construction or industrial accidents, and more.

The present invention will have an outer layer attached to the inner layer with a circular side layer housing an at compression impact sensor(s) measuring g-force and health data sensor(s) capture technology system, which could be one sensor data receiving or sending devices, and holding bracket device(s), which include(s) respectively for the health data system(s) a base member, a top member, and a continuous circular side member; and for the bracket member a top member, a base member, a square, rectangular, oval or circular member, a snap-in member(s), all of which in the health sensor(s) device, as well as the bracket device(s) respectively are or act as two engaged or connected units for function and medical data capture. The one complete unit, engaged as an impact and health capture data system. The additional sensor(s) if required are located "at compression" where impact force is measured at the point of impact or the point of compression versus in tension, and/or may be measured using Bluetooth inherently built into the sensor(s) system. The data capture system is to be applied as a health and impact force measurement unit system. The sensor bracket member(s) may use materials, such as impact resistant plastic, such as Polycarbonate, ABS, or other "plastic" materials used with a cavity to house or contain the sensor(s) therein. The bracket insert member(s) may also include or define a cavity, or cavities, numerous voids to house or hold the sensor(s). The sensor(s) member(s) house or include a computer circuit board that captures all the following metrics and more including: specific algorithms designed for this present invention, and may also include an impact crash and vitals sensor(s) system(s) to include data capture including, but not limited to: include an integrated micro or nano impact crash and vitals sensor(s) unit to track not only g-force, but also initial impact i.e. severity index, or "SI." Additionally, key vitals may also be tracked with an impact crash and vitals sensor(s) system in the sensor(s) system with a sensor(s) system that may be attached onto the skin or resting next to and touching the wearer's skin at the left temple that will measure blood pressure, oxygen saturation rate, heart rate, respiration rate, skin temperature, EKG, and more. Finally, the same system has fall or tripping detection, activity level, distance, location and altitude, speed, step count, and more. One feature of the present invention, is directed to the sensor(s) insert member, or specifically to the bracket housing or holding the sensor(s) member structure for sensor insert, the bracket structure comprising an outer member and a plurality of other outer members designed to securely hold the sensor(s) right next to the wearer's left temple, and the stability of the sensor(s) being held in place is also assisted by the helmet system with proper fit. The sensor is fully integrated into the wearer's helmet system and immediately engaging with the software on the sidelines held in a phone, tablet, laptop, computer, or some other hardware device that houses the software application and will capture real-time data transmitted by the sensor(s) housed in the wearer's helmetry system. Another feature of the present invention is directed to sensor itself, including top members, a base member, the continuous circular or round member, the computer member, the accelerometer(s) member(s), the gyro(s) member(s), the Bluetooth member (s), the radio frequency for transmission members, the ability to transmit data via/using the Cloud services member, the mathematical formulas or algorithms members designed for the capability of the present invention, the longitude or latitude members, and the proximity awareness member.

The base member structure includes an outer member and a plurality of a smooth impact engaging surface members designed throughout the base portion of the outer member. The top member structure includes an outer member and a plurality of a smooth impact engaging surface members designed throughout the top portion of the outer member. The circular side member structure includes an outer member and a plurality of a smooth impact engaging surface members designed throughout the circular or side portion of the outer member. Another feature of the invention is the plurality of the impact and health engaging members include a first impact and health engaging member in the base of the sensor(s) system, a second impact and health engaging member in the top of the sensor(s) system, and the third impact and health engaging member in the continuous circular or side member of the sensor(s) system, attached to or housed within the bracket system member. The plurality of members is unified into one member complete unit included and bounded by the first, second, and third engaging members. Another feature of the invention where the first impact and health engaging member, the second impact and health engaging member, and the third impact and health engaging member will also partially exhibit an impact capture motion through the use of the accelerometer sensor and gyro sensor members. Another feature of the invention is the plurality of all impact and health engaging members includes a second impact and health engaging member, where the entire second or top member is a second impact and health engaging member, which may also be termed as an apex. The second impact and health engaging member includes a first design and a second design, where the apex has a first height with respect to the base portion in the first design to follow the base design of the wearer's left temple. The height of the system may not be greater than the second height, where there is a subtle transition, not hard angled edges between the apex height and the base member. All impact and health engaging structure(s) at least partially comprises an impact resistant structure in the use of aforementioned material(s).

The current invention is an at compression impact and health data sensor capture technology systems that is designed to capture, record, and compare at compression impact g-force and the resultant effect on the wearer and the prospective issues resulting from the impact force. The current invention is designed to protect the wearer from prospective effects from one or more, repetitive impact force by providing the medical personnel real-time data from which to make a decision supported by comparative biometric vitals data rather than minimal assessments made on thousands of sidelines in enumerable sports, the military, or in construction or industrial accidents. The current invention, as an at compression impact and health data sensor capture technology system(s) where certain portions of which are included in a variety of form(s), such as "sensor (s)," "algorithms" "at compression," "and/or "at the point of impact," brackets," "hardware," "software," "app or applications," "sideline bio-metrics or vitals," as designed in the at compression impact and health data sensor capture technology system having an outer surface, an inner surface, a circular side surface, a front region bracket, a rear region bracket, an upper layer bracket, and two side region brackets.

Some aspects of the present invention relate generally to at compression impact and health data sensor capture technology systems for use in sporting activities, and other uses. The at compression impact and health data sensor capture technology systems using strategically placed sensor(s) that may occupy one or more placements within the helmet at the front, right & left sides, rear, and key locations in the soft headwear system of the impact and bio-metric vitals system. The sensor(s) may occupy one or more placement within the front, rear, and two sides of the impact engaging portion of the helmet shell system.

The at compression impact and health data sensor capture technology system may be formed from a variety of materials already in use in today's market, and may be formed with a variety of characteristics.

The at compression impact and health data sensor capture technology system may be formed from a variety of plastics, rubbers, synthetic, metals, precious metals, carbon fiber, composites, and more materials already in use in today's market, and may be formed with a variety of characteristics.

Aspects of the invention relate to athletic activity that incurs impact force when the wearer's helmet or soft headwear impacts the ground, another player, another helmet, an object, etc., whether it is through sports activities, as well as incurring a blast force for military personnel, dropped objects or falling persons on construction or industrial sites or locations, etc., and relates to at compression impact and health data sensor capture technology system means any device that houses the sensor(s) systems device, such as helmets, soft headwear, etc. directly addressing the wearer's head that incurs impact or g-force capturing, reading, and measuring the impact force, and also reading the wearer's bio-metric vitals data benching against resting data already recorded in software held in a receiving device, such as a computer, table, phone, etc. either held nearby on-field of play, or region, or by a remote medical professional to review in real-time. The at compression impact and health data sensor capture technology system receiving device, (i.e. a helmet or soft headwear system designed to read the g-force and bio-metric vital data from impacts), which is an at compression impact and health data sensor capture technology system and apparatus including a sensor(s) system with a top impact engaging member, base impact engaging member, a circular side impact engaging member, a bracket impact engaging member(s), with a sensor(s), the hardware, software, Cloud, Bluetooth, and more, plus a bracket housing member(s) that can withstand impact force, the sensor engaging members including at least a top member, and a base member, and a square, rectangular, oval, or circular side member, and at a bracket holding member(s), a system.

The at compression impact and health data sensor capture technology system three impact engaging member portions of the sensor(s) system contains the impact and health system, contained within the enclosed and sealed sensor will hold the hardware, mother board that contains the accelerometers, gyros, algorithms, all health data capture designed in the algorithms and code written into the software contained in the mother board hardware system, located next to the wearer's left temple region, and prospectively more/all distributed uniformly and throughout the entirety of the impact engaging helmet or soft headwear system of the sensor(s) system starting in the helmet or soft headwear system worn by the wearer, to the inside of the helmet shell member system, and/or embedded into the helmet shell member system. The depth of the helmet shell is no different from the prior art already in use in the marketplace, which typically is approximately $\frac{1}{8}^{th}$ of an inch in thickness when injection molded, approximately the same thickness when fabricated in a lay-up process system.

The bracket(s) housing the sensor(s) of an example embodiment of the invention may occupy up to 100% of the three impact engaging members portions of the sensor(s) top, base, and square, rectangular, oval, or circular sides engaging members of the at compression impact and health data sensor capture technology system.

As already described, the one or more protrusions included in the sensor(s) and bracket system(s) and the top or base impact engaging member of the sensor(s) system as an example of the embodiment of the invention, all of which may extend laterally, vertically, may have depth, may have height, and may be in three dimensional form.

Also as noted, the one or more protrusions included in the sensor(s) system and the top impact engaging member of the sensor(s) system as an example of the embodiment of the invention, all of which may extend laterally, vertically, may have depth, may have height, and may be in three dimensional form.

Also as noted, the one or more protrusions included in the sensor(s) system and the base impact engaging member of the sensor(s) system as an example of the embodiment of the invention, all of which may extend laterally, vertically, may have depth, may have height, and may be in three dimensional form.

Also as noted, the one or more protrusions included in the sensor(s) system and the circular side(s) impact engaging member of the sensor(s) system as an example of the embodiment of the invention, all of which may extend laterally, vertically, may have depth, may have height, and may be in three dimensional form.

Also as noted, the one or more protrusions included in the sensor(s) system and the impact crash and vitals sensor(s) lead system of the embodiment of the invention, all of which may extend laterally, vertically, may have depth, may have height, and may be in three dimensional form.

The sensor(s) system may be formed of a variety of materials and/or include a variety of features or element to alter or adjust characteristics of the sensor(s) impact receiving device. For example, the durable system may be formed out of some metal, including, but not limited to steel, galvanized steel, aluminum, titanium, carbon fiber, graphene, fiberglass, a composite of materials, and more use of materials as in the prior art.

The sensor(s) bracket system(s) may be formed of a variety of materials and/or include a variety of features or element to alter or adjust characteristics of the sensor(s) impact receiving device. For example, the pliable and durable system may be formed out of some polymer, such as flexible plastic, including, but not limited to plastics, thermoplastics including polyethylene, polypropylene, polystyrene, polyvinyl chloride, plus polytetrafluoroethylene, plus rubber, vulcanized neoprene, and more use of materials.

The impact crash and vitals sensor(s) system(s) may be formed from a variety of materials and form factors to address impact force, activity use, as well as address human vitals.

The impact crash and vitals sensor(s) portion of the sensor(s) system may be formed of a variety of materials from the prior art and/or include a variety of features or elements to alter or adjust characteristics of measurement of impact or g-force and prospectively severity impact, or "SI." This may be an off-the shelf material micro or nano form factor system utilized in other products.

Also as noted, the one or more protrusions included in the direct skin contact required for the vital monitoring sensor system engaging member of the sensor(s) system as an example of the embodiment of the invention, may have depth, may have height, and may be in a three dimensional form factor as designed or as used in the prior art. This may be an off-the shelf material micro or nano form factor system utilized in other products.

For example, to insert the sensor system where the sensor(s) strategically placed either in the helmet shell, or just behind on the inside in key strategic locations, such as the top, rear, right & left side of the helmet shell, wherein the sensor(s) has accelerometers sealed within the sensor(s) system, and wherein the accelerometer(s) is/are contained within the engaging impact members including the top member, base member, and circular side member(s).

To insert the sensor(s) system into the bracket system(s) wherein the sensor(s) are contained and snapped into within the engaging bracket impact members including the top member, base member, and square, rectangular, oval, or circular two sides members.

The impact crash and vitals sensor(s) system(s) contained in the sensor(s) system, wherein the Bluetooth system for transmission of data from the impact crash and vitals sensor (s) connect via wireless transmission to the sensor(s) health system software, and the sensor system is attached to the three impact engaging bracket members.

The impact crash and vitals sensor(s) system(s) contained in the sensor(s) system, wherein the leads from the impact crash and vitals sensor(s) combine to one lead member of the sensor(s) system, which is then snapped in or is attached to the three impact engaging bracket members with a lead wire extending out that may be snapped or plugged in at the apex of the three engaging bracket members specifically at the inside arch of the two side engaging members.

The impact crash and vitals sensor(s) system(s) contained in the sensor(s) system, wherein the leads from the impact crash and vitals sensor(s) combine to one lead member of the sensor(s) system is attached to the three impact engaging sensor members with a lead wire extending out that may be snapped or plugged in at the apex of the three engaging sensor members specifically at the inside arch and extending out several inches to attach to the wearers left temple region using a sticky or adhesive reusable pad, or may be incorporated into the liner system.

The sensor(s) system receiving device may be used in soft headwear, such as headbands, skullcaps, and for use in military helmets, construction/industrial helmets and more.

Specific examples of the invention and the structures according to the examples of the invention are described in greater detail below. The reader of the invention should be aware that these specific examples and structures are set forth simply to illustrate the invention, and they should not be construed as limiting the invention.

Some aspects of the present invention relate generally to the wearers using head gear for protection from impacts and impact force, for helmets and soft headwear used for safety in athletic use, plus other uses. The sensor(s) system may occupy one or more placements within the helmet. The accelerometers sensor(s) system may occupy one or more placements within the helmet shell placed inside in key strategic locations, such as the top, rear, right & left side of the helmet shell, wherein the sensor(s) has accelerometers sealed within the sensor(s) system, and wherein the accelerometer(s) are contained within the engaging impact members including the top member, base member, and circular side member(s). The three engaging bracket members also contain or house the sensor(s). Sensors that capture impact force system, a sensor system capturing bio-metric vitals data, three engaging impact members and apparatus designed to house the sensor system in which g-force resulting from an impact force requires measurement. The bio-metrics captured in the sensor to be housed in a bracket, and placed next to the wearers left temple region touching the wearers skin, and where the accelerometer and gyro system is housed in the sensor next to the wearer's left temple, but also sensors with additional accelerometers may be strategically placed in the tip, rear, right and left sides of the helmet or soft headwear. The total engaging members of the sensor system housed in the bracket will capture all data required in order to know the number of hits taken by the wearer, the impact or g-force associated with sub-concussive to massive impacts, the bio-metrics taken immediately at the point of impact by the wearer and benched against data already contained in the application and software system in a computer, tablet, phone, or laptop held on the sidelines, in a booth at the arena or field of play, the off-field professional medical personnel, medics on the battlefield, foreman at construction sites, etc. The top, base, and circular side members, and made out of metal(s), including, but not limited to steel, galvanized steel, aluminum, titanium, carbon fiber, graphene, fiberglass, a composite of materials, and more use of materials as in the prior art. The bracket member may be made of plastics materials, including, but not limited to polyurethanes, polyolefins or any polymeric material, high density open cell urethane foam, a microcellular ethylene vinyl acetate (EVA) polyethylene foam, a viscoelastic plasticized polyurethane polymer, a viscoelastic urethane rubber polymer, a vulcanized neoprene, or other highly elastic materials able to withstand impact force, temperature changes also ensuring proper stability in function, or any polymeric material may occupy one or more placements within the sensor(s) system.

The at compression data sensor capture technology bracket system may be formed from a variety of plastic materials plastics, rubber, vulcanized neoprene, polyurethanes, polyolefins or any polymeric material, and more system may be formed from a variety of materials and may be formed with a variety of characteristics. The lead system may be formed from a variety of materials and may be formed with a variety of characteristics.

Aspects of the invention relate to athletic, military, construction/industrial use and relates to an at compression data sensor capture technology system, meaning the sensor(s) system that is placed in a helmet or soft headwear system will be next to the human or wearers left temple region preferably or other key locations to collect vital bio-metric data. The at compression data sensor capture technology system receiving device, (i.e., an at compression data sensor capture technology system designed to capture, read, analyze both impact or g-force data, as well as health data), which is an at compression data sensor capture technology system and apparatus including a sensor(s) system with three impact engaging member portions of the sensor(s) contains the impact and health sensor(s) system, housed within the bracket member system, independently, all distributed uniformly and throughout the entirety of the helmet system starting at the top of the helmet, the rear of the helmet, and the two sides of the helmet system. The impact crash and vitals sensor(s) system(s) portion contained within the top, base, and circular side engaging members will be placed to detect impact force and activity, vitals and fall detection.

The sensor(s) system receiving device when worn independently, preferably does present the user or a wearer with a normal feeling of fit, comfort, or the like. The sensor(s) is used to capture, read, and analyze both impact forces derived, as well as vital bio-metric data occurring at this impact from athletic or other use.

An example of the present invention of the impact and health sensor(s) system is comprised of sensor(s) contained or housed within a bracket and strategically placed at compression or at the point of impact in the helmet shell, and/or only at the wearer's left temple region to capture impact and resultant health data.

An at compression data sensor capture technology system device to be used for sports activities, military use, and construction or industrial use is described—impact force is taken at initial impact or compression at the impact's peak severity versus in tension at the wearer's head. Three impact engaging members housing the hardware, code, mother board, software, algorithms, accelerometers, gyros, g-force capture, health capture capabilities of key pertinent medical data usually taken at an emergency room or a doctor's office of the sensor(s) are designed with use of the aforementioned prior art patents with proven ability to read, capture and transmit health data, plus be able to read, capture, and transmit impact force taken at the point of impact or at compression versus in tension coupled with sensor(s) designed to read bio-metric vitals, vital signs/derivatives such as blood pressure, heart rate, oxygen saturation, respiration rate and skin temperature; enhanced vital signs, such as EKG, galvanic skin response, hydration, chronic disease management and alerts and pain level (provided by user); fitness tracking, such as activity level, ambient temperature, cellular head set, distance, fall detection, location and altitude, speed and step count; and impact force measurement, such as g-force and severity index.

All of the listed bio-metrics, of which are written into the software, hardware in the code using algorithms designed into the mother board specifically to capture these metrics, plus the sensor(s) will capture impact force at compression, in the helmet shell versus later in tension after the impact energy has translated through the liner system, and which there is no load distribution, no energy attenuation at impact or at compression, so the total energy is measured by the g-force at compression that is also at the point of peak severity of the acceleration, beginning of deceleration, linear and rotational impact forces. The impact and health sensor systems are encased in individual sensors the shape and approximate dimensions of between a U.S. minted nickel and quarter contained therein in each of the three impact engaging members (top, base, and side(s)) in the sensor(s) device that may be constructed from a number of impact resistant materials used in the prior art. A bracket member has the sensor snapped in with the bracket three engaging members to hold the sensor(s), which is easily secured inserted into current helmetry and the sensor is easily and rapidly removed/replaced. The bracket three impact engaging members include the top, base, and two sides of the prior art that may be constructed out of a number of materials from the prior art using polyurethanes, polyolefins, high density open cell urethane foam, a microcellular ethylene vinyl acetate (EVA) polyethylene foam, a viscoelastic plasticized polyurethane polymer, a viscoelastic urethane rubber polymer, a vulcanized neoprene, memory foam, or other highly elastic materials able to withstand impact force, temperature changes also ensuring proper stability in function, or any polymeric material. The bracket may be laminated, glued sewn, incorporated, or other fabrication methods into the liner system strategically positioned next to the wearer's left temple region, or a combination as used in the prior art. The sensor(s) may have an outer layer and an inner layer of solid yet flexible and durable impact resistant material from the prior art, and the sensors may also be attached to the helmet shell using a variety of fabrication methods including, but not limited to gluing, bonding, heat sealing, and other methods, as well as may be incorporated into the helmet shell production cycle directly. The health sensor top member must touch the wearer's skin preferably by the left temple region, or the neck region near the carotid artery. The lead wire(s) completes the sensor(s) system if required, and if Bluetooth is not used, or the leads/wires are in addition to the use of Bluetooth. The sensor(s) system(s) is used to determine impact force, as well as track physical vitals normally taken at the doctor's office or at the hospital, as well as athletic tracking of the number of steps, activity levels, and finally potential fall or tripping detection to alert others of the individuals falling/pitching associated with concussions, plus more.

The sensor(s) wherein the sensor three impact engaging members comprised of the top, base, and circular side members construction for the sensor(s) contains therein the key software, code, hardware, mother board, algorithms, accelerometers, gyros, and more to measure impact force and key health vital bio-metrics.

The sensor(s) where each of the sensors hold the key software, code, hardware, mother board, algorithms, accelerometers, gyros, and more to measure impact force and key health vital bio-metrics in a completely enclosed environment.

The sensor(s) where the sensor comprises a pre-shaped or designed system shaped like a coin via construct or form factor using three impact engaging members containing the sensor(s) internal system with memory, codes, algorithms, accelerometers, gyros, and more.

The sensor(s) where the sensor is sealed with an inner or top layer, and an outer or bottom layer with a circular side layer to completely enclose and seal the sensor cell into one complete unit containing the sensors internal system, and is contained within a pre-shaped or designed system shaped like a coin in the shapes of the three impact engaging members of the sensor(s). The sensor(s) where the sensor with the internal system is held in place by a bracket designed with three impact engaging members. The sensor(s) having the bracket securement on the inside of the helmet shell in strategic location of front, rear, and two sides a first layer using adhesive, bonding or some other securement process forming the system of the impact sensor(s) device that contains the accelerometers and gyros. The sensor(s) having a top engaging member of the sensor(s) touching the wearer's left temple region, and touching the wearer's skin. The sensor(s) having a top engaging member of the sensor (s) secured and snapped into the bracket is securement into the liner system along the left temple region of the wearer. The sensor lead(s) having a connection to the accelerometers and the impact and health sensor.

The sensor(s) having an impact collection system, as well as a health bio-metrics vital data collection system using Bluetooth sent to the software system in a computer, tablet, phone, or laptop that is then transmitted through a Cloud-based portal for data transmission are contained within the code and software, as well as the hardware of the sensor internal system and then also may be transmitted to a third party.

The sensor(s) having a transmittal system using Bluetooth and the Cloud for data transmission are contained within the code and software, as well as the hardware of the sensor internal system. The sensor(s) also having an alert transmittal system using the Cloud for data transmission are contained within the code and software, as well as the hardware of the sensor internal system. The sensor(s) wherein at least one layer of the bracket three impact engaging members is comprised of materials from the prior art using polyurethanes, polyolefins, high density open cell urethane foam, a microcellular ethylene vinyl acetate (EVA) polyethylene foam, a viscoelastic plasticized polyurethane polymer, a viscoelastic urethane rubber polymer, a vulcanized neoprene, or other highly elastic materials able to withstand impact force, temperature changes also ensuring proper stability in function, or any polymeric material. The sensor (s) having a form factor that is prior art and materials of prior art to house the sensor internal system into one unit. The software of the sensor system is also downloadable as an "app," or "application." The sensor(s) having a Bluetooth capability to capture and transmit data on-field up to, but not limited to 1,000 yards to the software system. The sensor(s) having a wire lead and sensor(s) system(s) that attaches directly to the as part of the sensor portion of the lead and sensor(s) system(s).

The sensor(s) having the ability to monitor impact force, severity index, and potentially one or more of the following: heart rate, oxygen saturation rate, blood pressure, respiration rate, skin temperature, hydration, EKG, distance, fall and/or tripping detection, location and altitude, speed, and step count, plus more. The sensor(s) having the ability to measure impact force at the point of compression, or initial impact versus in tension.

An at compression data sensor capture technology system apparatus including a helmet with strategically placed accelerometer sensor(s) system with the sensor member(s), bracket that houses the sensor, bio-metrics vitals sensor(s), the faceguard, the ear ports, the Bluetooth capability, the liner system, the wearer's left temple region, sensor accelerometers embedded into the helmet shell, and the sensor accelerometers placed directly inside the helmet shell, and lead connecting wires.

In a preferred embodiment, the protective sensor(s) are comprised of three impact engaging members containing a sensor, snapped into and/or secured to the helmet and liner system with a bracket system. The three impact engaging members having a top member, a base member, and a circular side member. The three impact engaging members having an outer, inner and circular layer(s) fabricated principally out of some form of impact resistant metal, or some similar material, with the layer members also containing a sensor system, with the sensor(s) member(s) also being housed in bracket member. The lead wires may be made of material to transmit energy signals, and the sensors embedded in the helmet shell, or just inside at the point of compression or at the point of impact. The three impact engaging members are all connected via being sealed, or some combination therein, and/or fabricated as one compete unit. The bracket system is either glued to the liner system, stitched into the liner system, is held in a pocket designed into the liner system, or some other form of attachment of the liner system, and is strategically located at the wearer's left temple region, in a preferred embodiment.

The various figures in the application illustrate examples of an at compression data impact and health sensor(s) capture technology system. Some of the figures show an apparatus and product comprised of and including sensor(s) system with three impact engaging members, Bluetooth use, and bracket member(s) used to house the sensor(s) independently. FIG. 3 shows the health and impact sensor system next to the wearer's left temple region, as well as shows attachment or positioning in the liner system, so as to be near or touching the wearer's skin. FIG. 4 shows the health and impact sensor system next to the wearer's left temple region. FIG. 5 shows the location of the impact sensors at compression either embedded in the helmet shell or right inside the helmet shell, and also in FIG. 5 shows lead lines, if required, attached from the sensors at compression, or point of impact, and the sensor system right next to the wearer's left temple region. FIG. 8 shows the proposed sensor(s) system data from capture to transmission to recordation route(s).

Other systems, methods, features and advantages of the embodiments will be, or will become, apparent to one of ordinary skill in the art upon examination of the following figures/illustrations and detailed description. It is intended that all such additional systems, methods, features and advantages be included within this description and this summary, be within the scope of the embodiments, and be protected by the following claims.

DETAILED DESCRIPTION OF THE PREFERRED EMBODIMENTS

Figure 1:
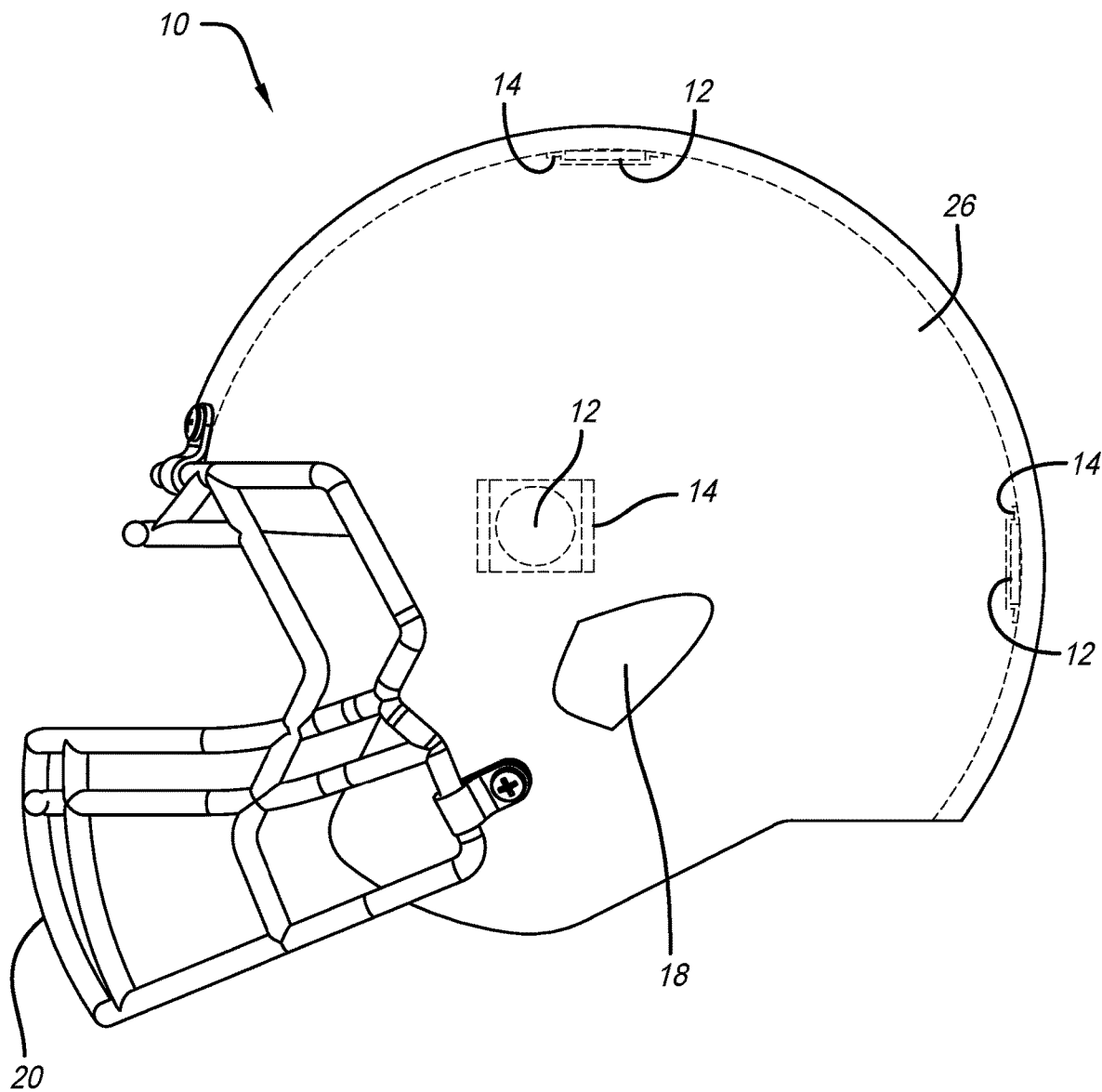
FIG. 1 is a schematic side view of a helmet in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the-disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

Referring now to the drawings, wherein the showings are for purposes of illustrating the present invention and not for purposes of limiting the same, FIGS. 1-8 show embodiments of a helmet and sensor system.

FIG. 1 illustrates the helmet 10 with the data collection system or sensor system having data collection assemblies 12 and bracket members 14 placed top, left side, and rear of the helmet shell 16. FIG. 1 also shows the ear ports 18 and the faceguard 20.

Figure 2:
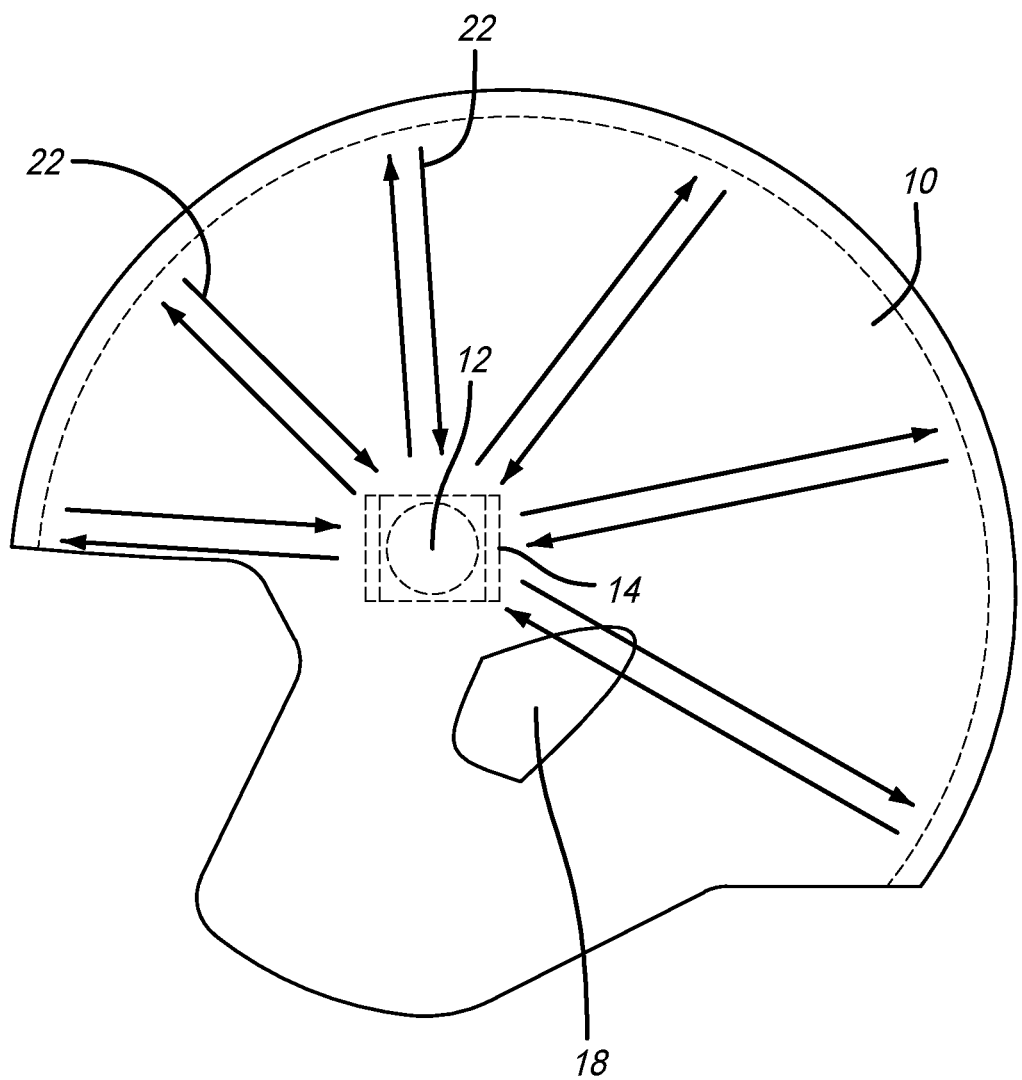
FIG. 2 is a schematic side view of the helmet showing data transmission.

FIG. 2 schematically illustrates the helmet 10 and the placement of the data collection assembly 12 of the system on the left side, and the bracket member 14, plus the direction of Bluetooth information flows (see arrows 22) sent from the data collection assemblies capturing the impact force at the point of impact or compression.

Figure 3:
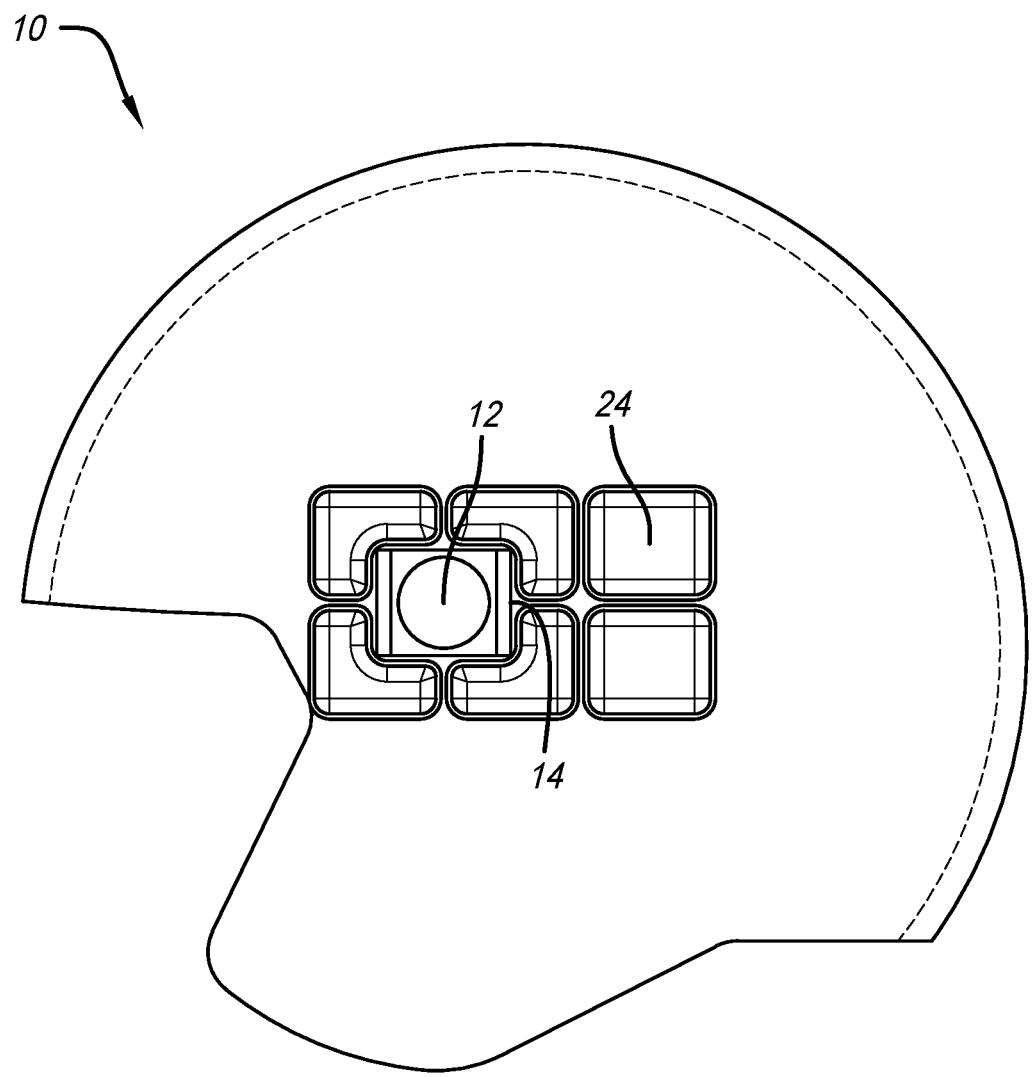
FIG. 3 is a schematic side view of the helmet showing the inner liner with the data collection assembly therein.

FIG. 3 schematically illustrates the helmet liner or inner liner system 24 with the bracket member 14 holding the data collection assembly 12 next to the wearer's head.

Figure 4:
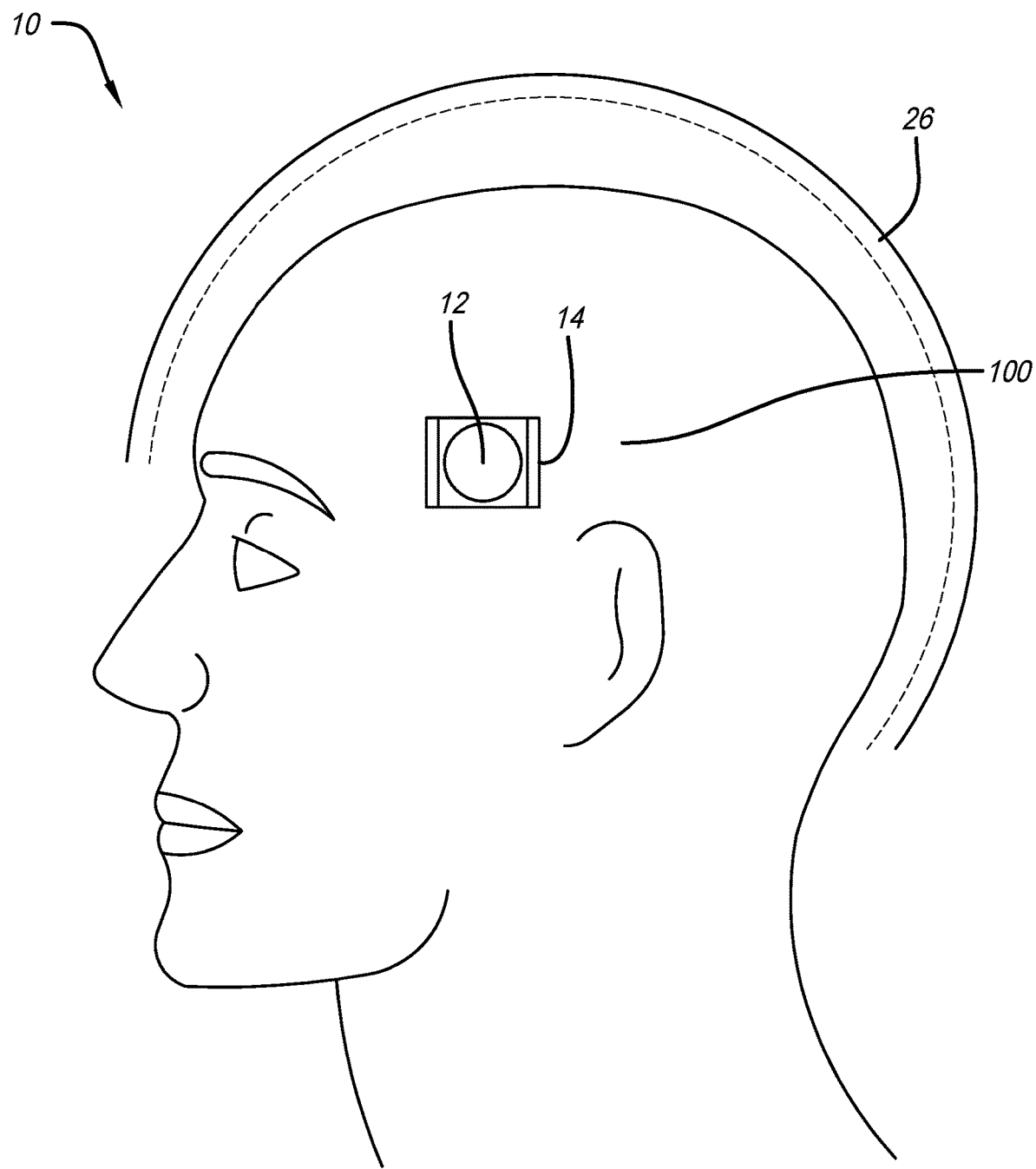
FIG. 4 is a schematic side view of the helmet showing the positioning of the data collection assembly adjacent the wearer's temple.

FIG. 4 illustrates the wearer's left temple region 100, and the placement of the data collection assembly 12 (which includes a bio-metrics vitals sensor) and the bracket member 14 next to the wearer's left temple region and directly addressing the wearer's skin (either against it or near thereto; both of which are considered adjacent herein).

Figure 5:
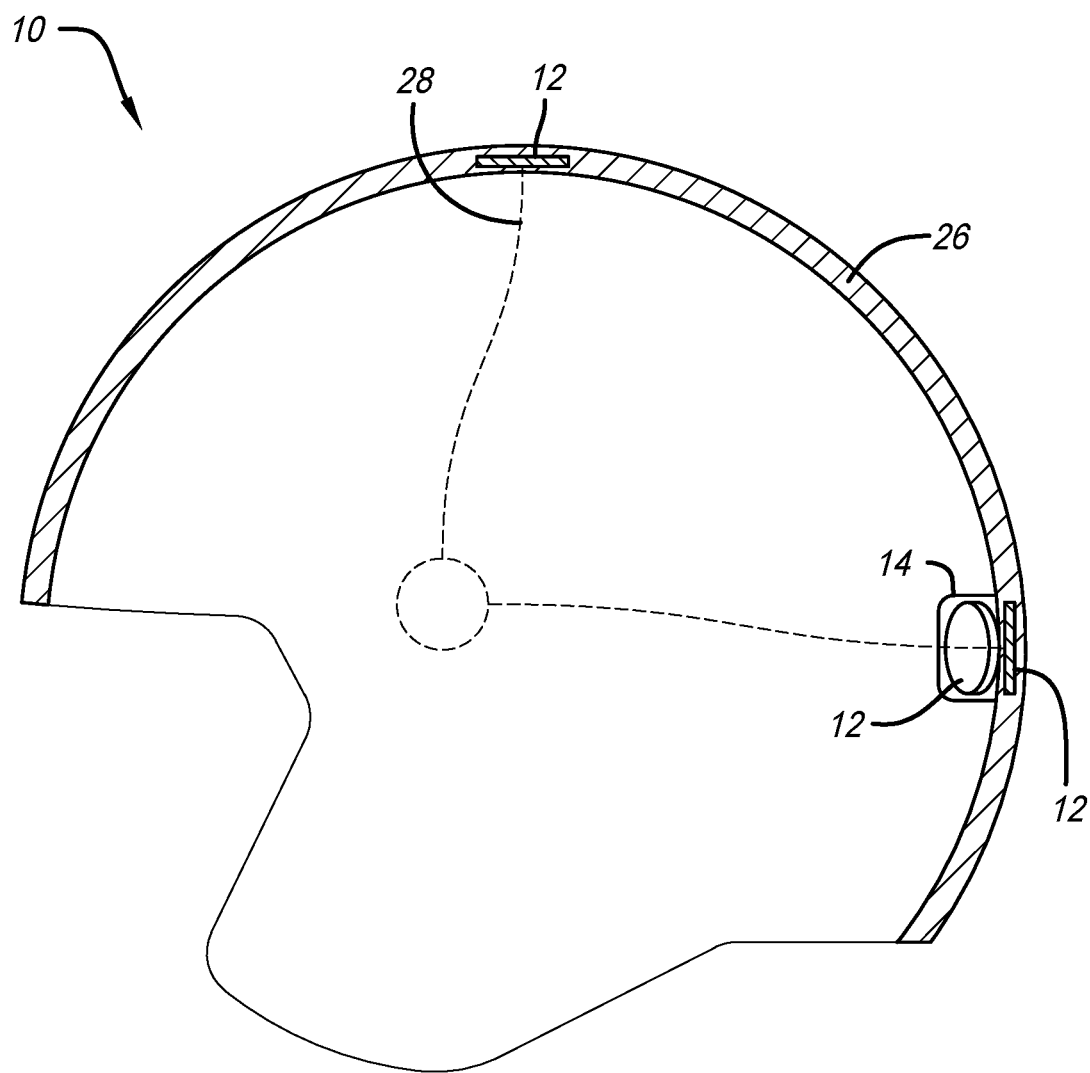
FIG. 5 is a cross-sectional schematic side view of the helmet showing lead wires.

FIG. 5 illustrates the helmet 10 demonstrating data collection assemblies 12 being embedded directly into the shell 26 itself of an either injection molded or lay-up helmet shell, as well as a data collection assembly 12 placed immediately inside the helmet shell 26, and shows optional lead wires 28 (wireless connectivity is also possible) from data collection assemblies placed in the helmet shell or just inside the helmet shell that are connected to the data collection assembly located at the wearer's left temple region.

Figure 8:
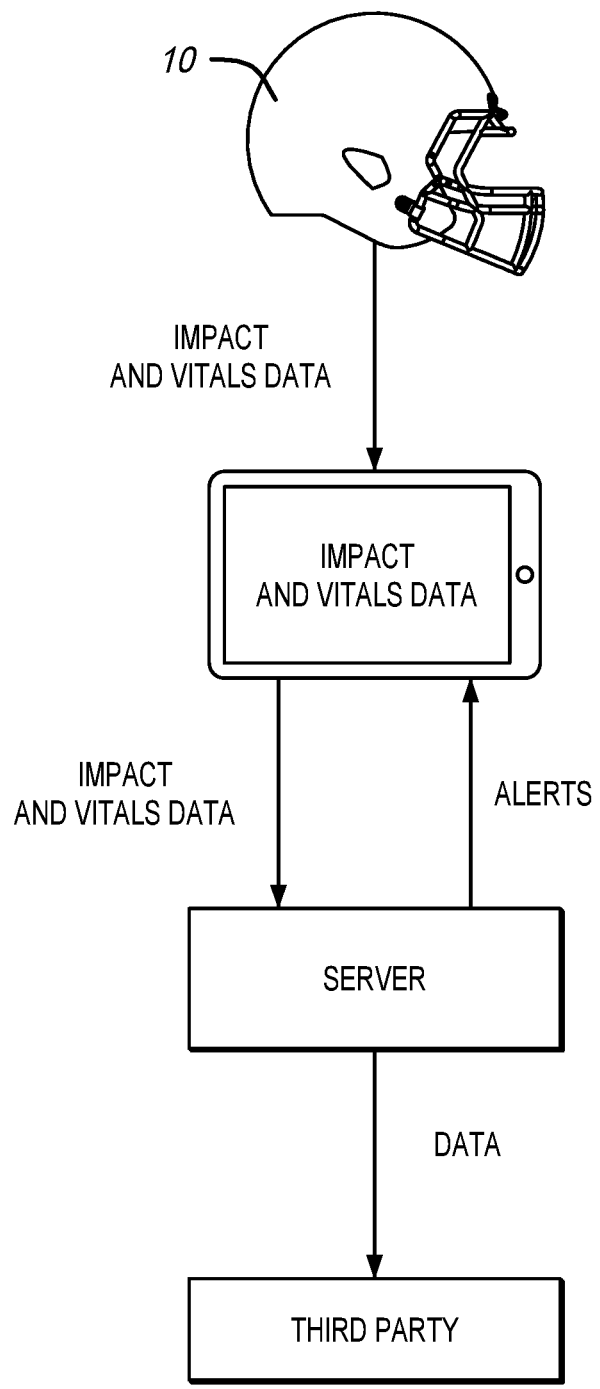
FIG. 8 is a flow chart showing the impact monitoring system in accordance with a preferred embodiment of the present invention.

FIG. 8 illustrates the sensor system demonstrating the data collection assemblies transmitting and receiving data, transmission to a server (e.g., via the cloud), transmission of the data to a third party (e.g., a hospital or the player's doctor), and real-time transmission to a portable mobile device (e.g., a tablet) that includes a corresponding software application (i.e., an "app") on the sidelines during the game, as well as in the receiving medical professionals computer, tablet, phone, etc.

Figure 6:
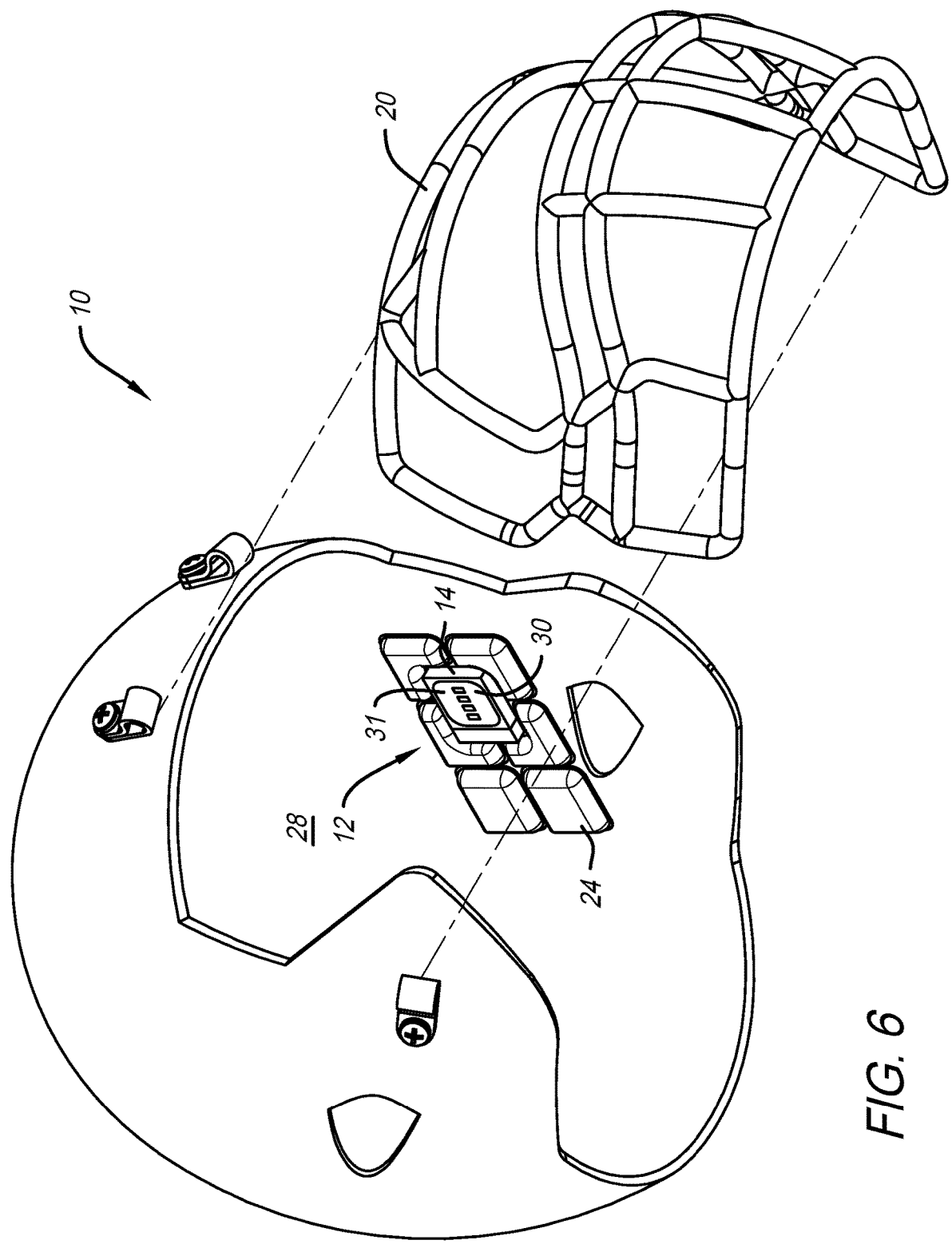
FIG. 6 is an exploded perspective view of the helmet showing the inner liner with the data collection assembly therein.
Figure 7:
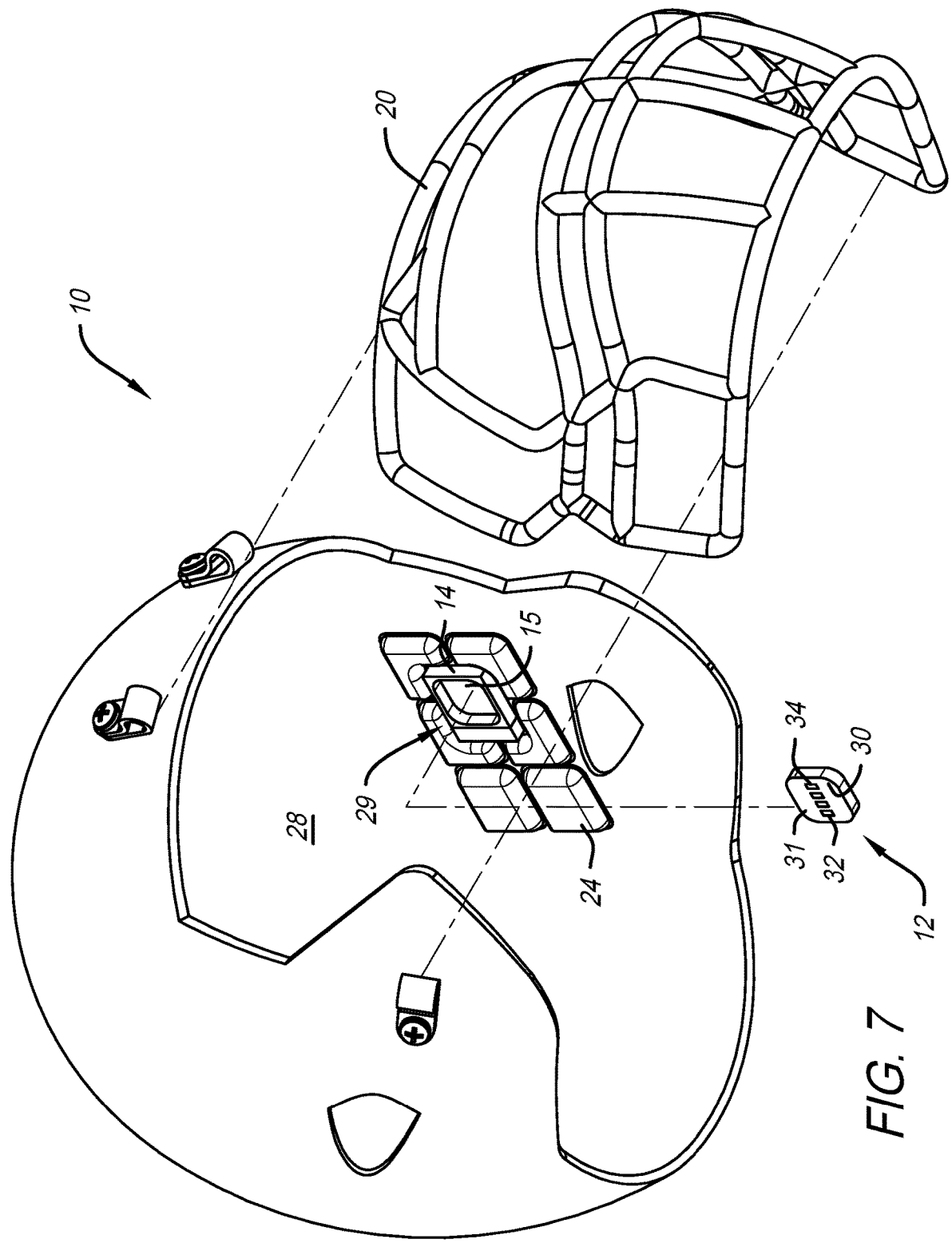
FIG. 7 is an exploded perspective view of the helmet showing the first housing exploded from the bracket.

FIG. 1 shows the helmet 10 (that is configured to be worn by a wearer) and that includes the outer shell 26, the inner liner 24 positioned inside the outer shell 26 and the data collection assembly 12, which includes one or more data collection sensors or members for measuring impact data, and one or more data collection sensors or members for measuring vital signs data. The data collection assembly 12 can be all of the sensors or data collection members within a single housing or encasement or can be a number of data collection members distributed throughout the helmet. As shown in FIGS. 6-7, the inner liner defines a liner interior 28 which is essentially where the wearer's head is positioned. It will be appreciated that the inner liner 24 extends throughout the interior of the helmet shell, but is only shown in one area in FIGS. 6-7 for simplicity. The inner surface of the inner liner 24 defines the liner interior 28. Preferably, the data collection assembly 12, includes a vital signs sensor 30 and the data collection assembly 12 is positioned such that vital signs sensor 30 is open to the liner interior 28, such that when the helmet 10 is worn by the wearer, the vital signs sensor 30 is positioned adjacent the wearer's skin. It will be appreciated that the vital signs sensor senses the vital signs and communicates it to the vital signs data collection member. In an embodiment, the vital signs sensor and the data collection member that collects the vital signs data may be the one and the same. The data collection assembly 12 can be positioned in a pocket 29 defined in the inner liner 24. In other words, the data collection assembly 12 is communicated with the liner interior 28 and positioned such that the vital signs sensor 30 is against or close to the wearer's skin when the helmet is worn. This allows the vital signs sensor 30 to sense the desired vital signs. The vital signs sensor can be any type of sensor or contact arrangement that senses a person's vital signs. For example, the vital signs sensor may be a sensor array that includes one or more optical emitters/transmitter devices 32 and one or more optical receivers/receiver devices 34 that are oriented to direct respective lights towards the wearer's body. The vital signs sensor can also include metal contacts or contacting the wearer's skin to collect the appropriate vital signs data.

As shown in FIGS. 6-7, in a preferred embodiment, the data collection assembly 12 is positioned in bracket 14 and is removable so that it can be replaced. The bracket 14, housing or frame defines a recess 15 into which the data collection assembly 12 is received. A button or the like can be included to release or pop the data collection assembly 12 out of the bracket 14. The bracket 14, housing or frame can also be wedged between pads in the liner system or otherwise incorporated into, but preferably not obstructing, the liner system. The data collection assembly 12 can include a battery therein (e.g., a rechargeable battery) to power the system. The data collection assembly 12 can also include electrical leads that connect with corresponding leads in the bracket 14 or within the helmet to provide power to any other components within the helmet.

In a preferred embodiment, the data collection assembly 12 also includes an impact or motion sensor that may comprise a multi-axis accelerometer, and/or a multi-axis gyroscope, and/or any other suitable device that can sense such values as pitch, roll, yaw, g-force, and other values or data as discussed herein. The accelerometer(s) and/or gyroscope(s) can be positioned anywhere in the helmet or liner and can communicate via Bluetooth or other wireless protocol (or can be wired, as shown in FIG. 5). The values or data prior to, during or after an impact event can be transmitted (via GPS and picked up via Bluetooth, for example) as shown in FIG. 8 (see "measured impact and vitals data").

In use, when an impact event occurs, an impact measurement is taken and impact data is collected. The impact measurement can include any or all of g-force, linear acceleration, rotational acceleration or any other data collected by the accelerometer(s) or gyro(s). A g-force measurement (along with other appropriate changes, such as linear or rotational acceleration, as discussed herein) is taken. If the impact measurement or the g-force measurement is above a predetermined value or threshold, a safety alert(s) is/are generated that is sent or communicated to the mobile electronic device on the sideline. The safety alert can also be generated on the mobile electronic device. Vital signs data is also collected and transmitted and is compared to resting benchmarks that were previously taken from the helmet wearer or individual player. If any of the collected vital signs data is above or below, as the case may be, a predetermined value or threshold, a safety alert may be generated. Fall sensing data can also be collected and measured (see, e.g., the '114 publication) and compared against benchmark data and a safety alert may be generated. In preferred embodiment, if the linear velocity measurement is above a predetermined value a safety alert may be generated. If the rotational velocity measurement is above a predetermined value a safety alert may be generated. The safety alerts can be an impact safety alert, a vital signs data alert, a particular vital signs safety alert (e.g., a blood pressure safety alert, a heart rate safety alert or any other vital sign discussed herein) or a combination safety alert where the impact data is compared to the vital signs data and if the impact data is at, above or within a certain threshold or threshold zone and one or more of the vital signs data is at, above or within a certain threshold or threshold zone, a safety alert is generated.

The wireless communication can include a wireless control unit that includes a wireless connectivity device that may be implemented in a wireless microcontroller unit. In an embodiment, the wireless control unit is a Bluetooth transceiver module configured to couple, via Bluetooth, to a remote device. In an embodiment, the Bluetooth module is a Bluetooth Low-Energy (BLE) module configured to be run in broadcast mode.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present invention. Other measurements or dimensions are within the scope of the invention.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. An impact monitoring system comprising:
    a helmet configured to be worn by a wearer, wherein the helmet includes
    an outer shell, an inner liner positioned inside the outer shell, wherein the inner liner defines a plurality of pad members that each include a pad outer surface, a pad inner surface, and a pad thickness defined between the pad inner surface and the pad outer surface, wherein the pad inner surfaces of the plurality of pad members define a liner interior, wherein a pocket is defined in one or more of the pad members, wherein a bracket is positioned in the pocket, wherein the bracket includes a recess defined therein, a data collection assembly that includes a first data collection member for measuring impact data, and a second data collection member for measuring vital signs data, wherein the first and second data collection members are housed in a first housing that includes a housing inner surface, a housing outer surface, and a housing thickness defined between the housing inner surface and housing outer surface, wherein the first housing is releasably received in the recess defined in the bracket, such that the housing inner surface is exposed to the liner interior such that the second data collection member can collect the current vital signs data, and wherein the housing thickness is less than the pad thickness, and a software application executing on a mobile electronic device in data communication with the data collection assembly, wherein when the impact data is at or above a predetermined threshold an impact safety alert is generated, wherein when a difference between the current vital signs data and previously collected resting vital signs data is at or above a predetermined threshold a vital signs safety alert is generated.

2. The impact monitoring system of claim 1 wherein the data collection assembly is positioned such that first housing is open to the liner interior, such that when the helmet is worn by the wearer, the vital signs sensor is positioned adjacent the wearer's skin.

3. The impact monitoring system of claim 2 wherein when the helmet is worn by the wearer, the first housing is positioned adjacent the wearer's temple region.

4. The impact monitoring system of claim 1 wherein the vital signs data includes one or more of blood pressure, oxygen saturation, heart rate, respiration rate, skin temperature, and EKG, and wherein the impact data includes one or more of g-force, linear acceleration, rotational acceleration and pitch changes, roll changes and yaw changes.

5. The impact monitoring system of claim 1 wherein the data collection assembly includes a third data collection member for measuring impact data, wherein the third data collection member is positioned outside of the first housing.

6. The impact monitoring system of claim 1 wherein the first housing is removable from the recess.

7. The impact monitoring system of claim 2 wherein the second data collection member includes at least one optical emitter and at least one optical receiver.

8. An impact monitoring system comprising:
a football helmet configured to be worn by a wearer, wherein the football helmet includes an outer shell, an inner liner positioned inside the outer shell, and a data collection assembly that includes a first data collection member for measuring impact data, and a second data collection member for measuring current vital signs data, wherein the inner liner defines a plurality of pad members that each include a pad outer surface, a pad inner surface, and a pad thickness defined between the pad inner surface and the pad outer surface, wherein the pad inner surfaces of the plurality of pad members define a liner interior, wherein a pocket is defined in one or more of the pad members, wherein a bracket is positioned in the pocket, wherein the bracket includes a recess defined therein, wherein the first and second data collection members are housed in a first housing that includes a housing inner surface, a housing outer surface, and a housing thickness defined between the housing inner surface and housing outer surface, wherein the first housing is releasably received in the recess defined in the bracket, such that the housing inner surface is exposed to the liner interior such that the second data collection member can collect the current vital signs data, and wherein the housing thickness is less than the pad thickness, and a software application executing on a mobile electronic device in data communication with the data collection assembly, wherein when the impact data is at or above a predetermined threshold an impact safety alert is generated, wherein when a difference between the current vital signs data and previously collected resting vital signs data is at or above a predetermined threshold a vital signs safety alert is generated.

9. The impact monitoring system of claim 8 further comprising a server in data communication with the mobile electronic device, wherein the impact safety alert is generated via the server.

10. The impact monitoring system of claim 8 wherein the impact data includes a g-force measurement, and wherein if the g-force measurement is above a predetermined threshold a g-force measurement safety alert is generated.

11. The impact monitoring system of claim 8 wherein when the helmet is worn by the wearer, the first housing is positioned adjacent the wearer's skin.

12. The impact monitoring system of claim 8 wherein the first housing includes a battery therein.

13. The impact monitoring system of claim 8 further comprising a button configured to release the first housing from the recess defined in the bracket.

14. The impact monitoring system of claim 12 wherein the plurality of pad members includes first, second, third and fourth pad members, wherein a first portion of the pocket is defined in the first pad member, a second portion of the pocket is defined in the second pad member, a third portion of the pocket is defined in the third pad member, and a fourth portion of the pocket is defined in the fourth pad member.

15. The impact monitoring system of claim 8 wherein the impact data is compared to the current vital signs data and when the impact data is at or above a certain threshold and the current vital signs data is at or above a predetermined threshold a combination safety alert is generated.

16. The impact monitoring system of claim 8 further comprising a third data collection member for detecting fall data, wherein when the fall data is at or above a predetermined threshold a fall safety alert is generated.

* * * * *